(12) United States Patent
York et al.

(10) Patent No.: US 10,016,517 B2
(45) Date of Patent: Jul. 10, 2018

(54) BIOACTIVE AMPHIPHILIC POLYMER STABILIZED NANOPARTICLES WITH ENHANCED STABILITY AND ACTIVITY

(75) Inventors: Adam W. York, Princeton, NJ (US); Prabhas V. Moghe, Basking Ridge, NJ (US); Kathryn E. Uhrich, Plainfield, NJ (US); Robert Prud'homme, Lawrenceville, NJ (US)

(73) Assignees: RUTGERS, THE STATE UNIVERSITY OF NEW JERSEY, New Brunswick, NJ (US); THE TRUSTEES OF PRINCETON UNIVERSITY, Princeton, NJ (US)

( * ) Notice: Subject to any disclaimer, the term of this patent is extended or adjusted under 35 U.S.C. 154(b) by 339 days.

(21) Appl. No.: 14/237,974

(22) PCT Filed: Aug. 8, 2012

(86) PCT No.: PCT/US2012/050040
§ 371 (c)(1),
(2), (4) Date: Jun. 10, 2014

(87) PCT Pub. No.: WO2013/023003
PCT Pub. Date: Feb. 14, 2013

(65) Prior Publication Data
US 2014/0328763 A1    Nov. 6, 2014

Related U.S. Application Data

(60) Provisional application No. 61/521,116, filed on Aug. 8, 2011.

(51) Int. Cl.
| | | |
|---|---|---|
| A61K 9/14 | (2006.01) |
| A61K 49/00 | (2006.01) |
| G01N 33/92 | (2006.01) |
| A61L 27/18 | (2006.01) |
| A61L 27/54 | (2006.01) |
| A61L 29/16 | (2006.01) |
| A61L 31/16 | (2006.01) |
| A61K 9/51 | (2006.01) |
| A61K 47/54 | (2017.01) |
| A61K 47/64 | (2017.01) |
| A61K 47/69 | (2017.01) |

(52) U.S. Cl.
CPC .......... *A61K 49/0093* (2013.01); *A61K 9/513* (2013.01); *A61K 47/542* (2017.08); *A61K 47/6425* (2017.08); *A61K 47/6907* (2017.08); *A61K 49/0082* (2013.01); *A61L 27/18* (2013.01); *A61L 27/54* (2013.01); *A61L 29/16* (2013.01); *A61L 31/16* (2013.01); *G01N 33/92* (2013.01); *A61K 9/14* (2013.01); *A61K 9/141* (2013.01); *A61K 9/51* (2013.01); *A61L 2300/44* (2013.01); *A61L 2300/442* (2013.01); *A61L 2300/624* (2013.01); *A61L 2400/12* (2013.01)

(58) Field of Classification Search
None
See application file for complete search history.

(56) References Cited

U.S. PATENT DOCUMENTS

| | | | | |
|---|---|---|---|---|
| 6,638,494 B1 * | 10/2003 | Pilgrimm | ............ | A61K 9/5094 424/490 |
| 2009/0048201 A1 | 2/2009 | Bednarski et al. | | |
| 2010/0330368 A1 | 12/2010 | Prud'homme et al. | | |
| 2011/0008396 A1 | 1/2011 | Moghe et al. | | |
| 2011/0229416 A1 | 9/2011 | Uhrich et al. | | |

FOREIGN PATENT DOCUMENTS

WO    WO 2009039505 A1 *  3/2009  ............ A61K 31/40

OTHER PUBLICATIONS

York et al., "Kinetically Assembled Nanoparticles of Bioactive Macromolecules Exhibit Enhanced Stability and Cell-Targeted Biological Efficacy", Jan. 2, 2012, Advanced Materials, vol. 24, Is 6, p. 733-739.

* cited by examiner

*Primary Examiner* — James W Rogers
(74) *Attorney, Agent, or Firm* — Fox Rothschild LLP

(57) ABSTRACT

The present invention relates to nanoparticle compositions and treatment of cardiovascular disease using nanoparticles to target Class A and B scavenger receptors. This invention further relates to methods of detecting cells that express scavenger receptors, detecting atherosclerotic lesions, and targeting bioactive amphiphilic macromolecules to cells that express scavenger receptors.

3 Claims, 6 Drawing Sheets

BIOACTIVE AMPHIPHILIC POLYMER STABILIZED NANOPARTICLES WITH ENHANCED STABILITY AND ACTIVITY

This application claims priority to U.S. Provisional Patent Application Ser. No. 61/521,116, filed on Aug. 8, 2011, the disclosure of which is incorporated herein by reference in its entirety.

STATEMENT REGARDING FEDERALLY SPONSORED RESEARCH

This invention was made with government support under NIH R21HL093753 and NIH T32EB005583 awarded by the National Institutes of Health. The federal government has certain rights in this invention.

BACKGROUND OF THE INVENTION

Cardiovascular disease (CVD) is the leading cause of death in western countries. Atherosclerosis is a condition involving the accumulation of lipid-rich plaques and chronic inflammation of the vascular wall. Plaque deposits initiate when low-density lipoproteins (LDL) accumulate in the artery wall and subsequently undergo oxidative modification (oxLDL). OxLDL stimulates endothelial inflammation triggering monocyte recruitment and subsequent monocyte differentiation to macrophages. Intimal macrophages exhibit unregulated uptake of oxLDL, via scavenger receptors, leading to the formation and accumulation of lipid laden macrophages (foam cells), which in turn drives plaque development. Class A and B scavenger receptors account for 75 to 90% uptake of modified LDLs. Development of a targeted and shielded therapeutic for managing atherosclerosis is needed.

SUMMARY OF THE INVENTION

The present invention relates to nanoparticle compositions and treatment of cardiovascular disease using nanoparticles to target Class A and B scavenger receptors. This invention further relates to methods of detecting cells that express scavenger receptors, detecting atherosclerotic lesions (also known as plaque), and targeting bioactive amphiphilic macromolecules to cells that express scavenger receptors. Development of a targeted and shielded therapeutic for managing atherosclerosis is needed.

One embodiment of the present invention is a nanoparticle comprising a hydrophobic core and a bioactive amphiphilic macromolecule coating said core and comprising a hydrophobic segment and a hydrophilic segment; wherein said nanoparticle comprises a single hydrophobic phase consisting of said hydrophobic core and said hydrophobic segment of the bioactive amphiphilic macromolecule; wherein the hydrophobic core and the bioactive amphiphilic macromolecule are selected so said hydrophobic core and the hydrophobic segment of said bioactive amphiphilic macromolecule are miscible in the hydrophobic phase. In a further embodiment of the invention, the nanoparticle may further comprise a ratio by weight 2:1, bioactive amphiphilic macromolecule to hydrophobic core.

An embodiment of the present invention is a nanoparticle wherein the hydrophobic core is represented by Formula A:

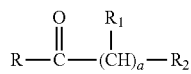

$R=-NHR_4$ or $-OR_4$
$R_1=-OR_3$ or $-OC(=O)C(CH_2OR_3)_2(CH_3)$
$R_2=H, CH_3, OH$ or $COR$
$R_3=H$ or $C(=O)OR_5$
$R_4=C_1-C_5$ alkyl or H
$R_5=$ a saturated or unsaturated alkyl chain having 10-20 carbon atoms.
$a=2-8$ An embodiment of the present invention is a nanoparticle wherein the bioactive amphiphilic macromolecule is represented by Formula B:

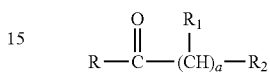

$R=NHR_4, OR_4$
$R_1=-OR_3$ or $-OC(=O)C(CH_2OR_3)_2(CH_3)$

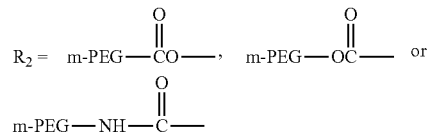

$R_3=H$, or $C(=O)OR_5$
$R_4=C_1-C_5$ alkyl, H, $C_1-C_3NH_2$, $(CH_2)_bCOOH$, $(CH_2)_aNHC(=O)(CH_2)_aR_1C(=O)R$ or $C_6H_4R_6$
$R_5=$ a saturated or unsaturated alkyl chain having 10-20 carbon atoms.
$R_6=(COOH)_c$ or H
$a=2-8$
$b=1-5$
$c=1-2$ In certain embodiments, the nanoparticle may be represented by $R=OR_4$, $R_1=-OR_3$, $R_2=$m-PEG-COOH, $R_3=C(=O)R_5$, $R_4=C_3$ alkyl, $R_5=$a saturated alkyl chain having 10-20 carbon atoms and $a=4$.

In certain embodiments, the nanoparticle may be represented by $R=NHR_4$, $R1=-OR_3$, $R_2=$m-PEG-COOH, $R_3=C(=O)R_5$, $R_4=C_6H_4R_6$, $R_5=$a saturated alkyl chain having 10-20 carbon atoms, $R_6=(COOH)_c$, $a=4$ and $c=2$.

In certain embodiments, the nanoparticle may be represented by $R=NHR_4$, $R1=-OR_3$, $R_2=$m-PEG-COOH, $R_3=C(=O)R_5$, $R_4=C_2NH_2$, and $a=4$.

The present invention provides a pharmaceutical composition comprising one or more nanoparticles comprising a hydrophobic core and a bioactive amphiphilic macromolecule coating said core and comprising a hydrophobic segment and a hydrophilic segment; wherein said nanoparticle comprises a single hydrophobic phase consisting of said hydrophobic core and said hydrophobic segment of the bioactive amphiphilic macromolecule; wherein the hydrophobic core and the bioactive amphiphilic macromolecule are selected so said hydrophobic core and the hydrophobic segment of said bioactive amphiphilic macromolecule are miscible in the hydrophobic phase. In a further embodiment, the pharmaceutical composition comprises one or more nanoparticles comprising Formula A and B. In a further embodiment, the pharmaceutical composition may further comprise at least one diagnostic or targeting agent, or both. In a further embodiment, the pharmaceutical composition may further comprise a pharmaceutically acceptable carrier.

The present invention provides a method to reduce the uptake of oxidized low-density lipoproteins in a subject with atherosclerosis comprising administering a therapeutically effective amount of at least one pharmaceutical composition comprising one or more nanoparticles comprising a hydrophobic core and a bioactive amphiphilic macromolecule coating said core and comprising a hydrophobic segment and a hydrophilic segment; wherein said nanoparticle comprises a single hydrophobic phase consisting of said hydrophobic core and said hydrophobic segment of the bioactive amphiphilic macromolecule; wherein the hydrophobic core and the bioactive amphiphilic macromolecule are selected so said hydrophobic core and the hydrophobic segment of said bioactive amphiphilic macromolecule are miscible in the hydrophobic phase. In a further embodiment, the pharmaceutical composition comprises one or more nanoparticles comprising Formula A and B.

The present invention provides a method of preventing or treating atherosclerosis comprising the steps of identifying a patient in need of such prevention or treatment, and administering to said patient a therapeutically effective amount of at least one pharmaceutical composition comprising one or more nanoparticles comprising a hydrophobic core and a bioactive amphiphilic macromolecule coating said core and comprising a hydrophobic segment and a hydrophilic segment; wherein said nanoparticle comprises a single hydrophobic phase consisting of said hydrophobic core and said hydrophobic segment of the bioactive amphiphilic macromolecule; wherein the hydrophobic core and the bioactive amphiphilic macromolecule are selected so said hydrophobic core and the hydrophobic segment of said bioactive amphiphilic macromolecule are miscible in the hydrophobic phase. In a further embodiment, the pharmaceutical composition comprises one or more nanoparticles comprising Formula A and B. In a further embodiment, the therapeutically effective amount of the pharmaceutical composition is administered parenterally, intravenously, intra-arterially, intra-peritoneally, intra-muscularly, subcutaneously or is administered locally from a drug eluting stent.

The present invention provides a biomedical device comprising a pharmaceutical composition comprising one or more nanoparticles comprising a hydrophobic core and a bioactive amphiphilic macromolecule coating said core and comprising a hydrophobic segment and a hydrophilic segment; wherein said nanoparticle comprises a single hydrophobic phase consisting of said hydrophobic core and said hydrophobic segment of the bioactive amphiphilic macromolecule; wherein the hydrophobic core and the bioactive amphiphilic macromolecule are selected so said hydrophobic core and the hydrophobic segment of said bioactive amphiphilic macromolecule are miscible in the hydrophobic phase. In a further embodiment, the pharmaceutical composition comprises one or more nanoparticles comprising Formula A and B. In a further embodiment, a biomedical device may be a stent, a catheter, a prosthetic valve, a cardiac valve, or a venous valve.

The present invention provides a method to detect a scavenger receptor or a CD 36 receptor expressed by a cell comprising contacting a cell with a pharmaceutical composition comprising one or more nanoparticles comprising a hydrophobic core and a bioactive amphiphilic macromolecule coating said core and comprising a hydrophobic segment and a hydrophilic segment; wherein said nanoparticle comprises a single hydrophobic phase consisting of said hydrophobic core and said hydrophobic segment of the bioactive amphiphilic macromolecule; wherein the hydrophobic core and the bioactive amphiphilic macromolecule are selected so said hydrophobic core and the hydrophobic segment of said bioactive amphiphilic macromolecule are miscible in the hydrophobic phase, wherein said pharmaceutical composition further comprises a diagnostic agent. In a further embodiment, the pharmaceutical composition comprises one or more nanoparticles comprising Formula A and B, wherein said pharmaceutical composition further comprises a diagnostic agent. In a further embodiment, the scavenger receptor may be SCARA1, SCARA2, SCARA3, SCARA4, SCARA5, SCARB1, SCARB2 or SCARB3.

The present invention further provides a method to detect a scavenger receptor or a CD 36 receptor in a subject comprising administering to a subject a pharmaceutical composition comprising one or more nanoparticles comprising a hydrophobic core and a bioactive amphiphilic macromolecule coating said core and comprising a hydrophobic segment and a hydrophilic segment; wherein said nanoparticle comprises a single hydrophobic phase consisting of said hydrophobic core and said hydrophobic segment of the bioactive amphiphilic macromolecule; wherein the hydrophobic core and the bioactive amphiphilic macromolecule are selected so said hydrophobic core and the hydrophobic segment of said bioactive amphiphilic macromolecule are miscible in the hydrophobic phase, wherein said pharmaceutical composition further comprises a diagnostic agent. In a further embodiment, the pharmaceutical composition comprises one or more nanoparticles comprising Formula A and B, wherein said pharmaceutical composition further comprises a diagnostic agent. In a further embodiment, the scavenger receptor may be SCARA1, SCARA2, SCARA3, SCARA4, SCARA5, SCARB1, SCARB2 or SCARB3.

The present invention provides a method to target atherosclerotic lesions and inflammatory vasculature in a subject comprising administering a pharmaceutical composition comprising one or more nanoparticles comprising a hydrophobic core and a bioactive amphiphilic macromolecule coating said core and comprising a hydrophobic segment and a hydrophilic segment; wherein said nanoparticle comprises a single hydrophobic phase consisting of said hydrophobic core and said hydrophobic segment of the bioactive amphiphilic macromolecule; wherein the hydrophobic core and the bioactive amphiphilic macromolecule are selected so said hydrophobic core and the hydrophobic segment of said bioactive amphiphilic macromolecule are miscible in the hydrophobic phase. In a further embodiment, the pharmaceutical composition comprises one or more nanoparticles comprising Formula A and B, wherein said pharmaceutical composition further comprises a targeting agent. In a further embodiment, the pharmaceutical composition further comprises a targeting agent. In a further embodiment, the targeting agent may be vascular adhesion molecule-1 (VCAM-1) peptide or Intercellular Adhesion Molecule 1 (ICAM-1) peptide.

BRIEF DESCRIPTION OF THE DRAWINGS

FIG. 1(A) Schematic of physical property differences between thermodynamic micelle assemblies by aqueous dissolution above the critical micelle concentration (top) and kinetic assembled NPs formulated by Flash NanoPrecipitation (bottom). FIG. 1(B) Schematic of Flash NanoPrecipitation and process requirements for colloidal stable NPs. $\tau_{mix}$ represents the time required for complete and homogenous mixing of the aqueous and solvent stream, while $\tau_{flash}$ is the precipitation or NP formation time. FIG. 1(C) Table listing the chemical structures of amphiphilic macromolecules (AMs) and core organic solutes, AM to core solute weight ratios investigated, NP acronyms, and hydrodynamic diameters ($D_h$) and polydispersity indices (PdI or PDI) as determined by dynamic light scattering. Data are from an n=3-5 conducted in triplicate with error representing ±S.E.M.

FIG. 2(A) Intensity distribution of 1CM/M12 10/5 NPs stored at 37° C. for 4 weeks. Hydrodynamic diameters ($D_h$) and polydispersity indices (PdI) are listed next to the respective sample. FIG. 2(B) Intensity distribution of 1CM/M12 10/5 NPs incubated with 20% fetal bovine serum (FBS) at time zero and 24 h. NP incubation under serum-free conditions is plotted for reference. FIG. 2(C) The release of 1CM from kinetically fabricated NPs (black symbols) versus thermodynamically assembled micelles (red symbols) is reduced when dialyzed under sink conditions against PBS (open symbols) or PBS+10% FBS (closed symbols). The release of fluorescein labeled 1CM (20% by weight) was monitored via UV-vis spectroscopy for both systems.

FIG. 3(B) Quantification of DiO oxLDL (5 μg mL$^{-1}$) uptake by MDMs after 24 h incubation with 1CM micelles or 1CM/M12 NPs under 0 to 20% FBS, [1CM]=10$^{-6}$ M. PEG-b-PLA/PLA 10/5 NPs serve as an inactive control and all treatments are normalized to cells incubated exclusively with DiO oxLDL. FIG. 3(C) Quantification of bright field images of foam cell phenotype after 48 h incubation of MDMs with no oxLDL (Basal), oxLDL, 1CM micelles+oxLDL, or 1CM/M12 10/5 NPs+oxLDL with 10% FBS ([oxLDL]=50 μg mL$^{-1}$, [1CM]=10$^{-5}$ M). Foam cells were quantified using OilRed O (red) staining and marking cell nuclei with Hoechst 33342. Data for FIG. 3(B) and FIG. 3(C) are from an n=3 conducted in triplicate (error bars=±S.E.M.). FIG. 3(B), statistical significance was evaluated at p<0.05, * indicates significance versus PEG-b-PLA/PLA 10/5 NP and # versus 1CM micelles. FIG. 3(C), statistical significance was evaluated at p<0.05, * indicates significance versus oxLDL and # versus Basal conditions.

DETAILED DESCRIPTION OF THE INVENTION

Figure 1:
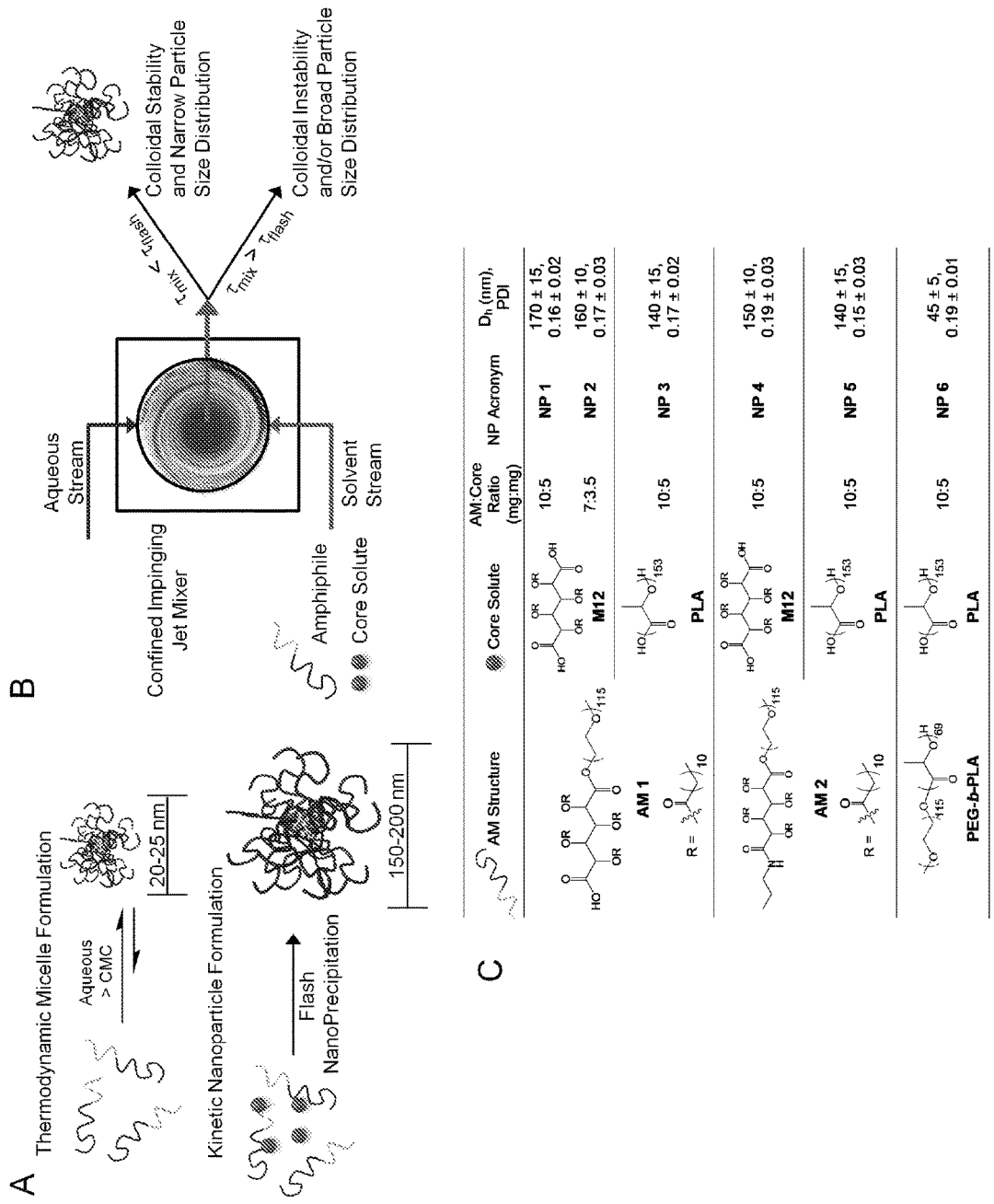
FIG. 1 depicts: Kinetically assembled nanoparticles (NPs) of bioactive macromolecules fabricated via Flash NanoPrecipitation.

The present invention relates to nanoparticle compositions and treatment of cardiovascular disease using nanoparticles to target Class A and B scavenger receptors. This invention further relates to methods of detecting cells that express scavenger receptors on the surface of the cell, detecting atherosclerotic lesions (also known as plaque), and targeting bioactive amphiphilic macromolecules to cells that express scavenger receptors.

Nanoparticle Composition

Flash NanoPrecipitation, yields kinetically assembled organic nanoparticles (NPs), as depicted in FIG. 1A. NPs prepared by this technique display a greater resistance to particle dissolution and allow higher bioactive loading capacities in comparison to traditional micellar constructs. The Flash NanoPrecipitation (FP) process is highlighted in FIG. 1B and involves the rapid mixing of an aqueous stream with a water-miscible organic solvent stream containing hydrophobic solutes and amphiphilic macromolecules (AMs). Rapid mixing generates supersaturation of the hydrophobic solute in the anti-solvent stream, which induces nucleation and NP growth. Hydrophobic functionalities of the AM are also incorporated during growth. To ensure uniform kinetics and thus a homogenous NP size distribution, the time of mixing both streams, $\tau_{mix}$, must be less than the NP formation time, $\tau_{flash}$, or in other words the induction times of both AM aggregation and precipitation/nucleation of the core solute. In addition to having $\tau_{mix} < \tau_{flash}$, the solubilities of the AM hydrophobe and the core components must be properly matched, otherwise the rate of precipitation of either component will not proceed in tandem leading to colloidal instability and/or broad diameter distributions. Employing AMs and core forming hydrophobic solutes of matching hydrophobicities, supports favorable mixing and imbeds the AM into the NP core. The NPs posses the ability to bind a scavenger receptor and inhibit the uptake of oxLDL and foam cell formation in human monocyte-derived macrophages (MDMs), both of which are key components in the progression and development of atherosclerotic lesions.

The term phase refers to a region of space, throughout which all physical properties of a material are essentially uniform. Phases may also be differentiated based on solubility as in polar (hydrophilic) or non-polar (hydrophobic). A mixture of water (a polar liquid) and oil (a non-polar liquid) will spontaneously separate into two phases. Here, the NP comprises a hydrophobic core and an AM that does not spontaneously separate into two phases and is characterized by a single hydrophobic phase. The AM contains a hydrophilic and a hydrophobic segment. The hydrophobic segment of the AM essentially coats the core of the NP, because the hydrophobic segment of the AM is physically embedded into the NP core by the physical means of Flash NanoPrecipitation. The AM is not bound chemically nor thermodynamically to the NP core. The AM can be considered to be frozen or locked to the NP core. The term miscible refers to the ability to be mixed into a uniform solution or phase.

A bioactive nanoparticle produced by FP comprises of a hydrophobic core and a bioactive amphiphilic macromolecules (bAMs). The bAM contains a hydrophilic and a hydrophobic segment. The hydrophobic segment of the bAM essentially coats the core of the NP, because the hydrophobic segment of the AM is physically embedded into the NP core by the physical means of Flash NanoPrecipitation. In a preferred embodiment the hydrophobic core and the bAM solubilities are properly matched. In other words, the hydrophobic segment of the bAM is properly matched to the hydrophobic core. In a preferred embodiment, a NP comprises a hydrophobic core and a bioactive amphiphilic macromolecule coating said core and comprising a hydrophobic segment and a hydrophilic segment; wherein said nanoparticle comprises a single hydrophobic phase consisting of said hydrophobic core and said hydrophobic segment of the bioactive amphiphilic macromolecule; wherein the hydrophobic core and the bioactive amphiphilic macromolecule are selected so said hydrophobic core and the hydrophobic segment of said bioactive amphiphilic macromolecule are miscible in the hydrophobic phase. The NPs of the present invention range in diameter from 100 nm to 500 nm.

As used herein, a "hydrophobic core" is a hydrophobic molecule that is insoluble in aqueous solutions. The molecule may be without limitation a polymer, a carbohydrate, or a chain of peptides.

In another embodiment of the present invention, a hydrophobic core is represented by the following. Formula A:

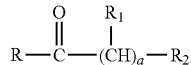

R=—NHR$_4$ or —OR$_4$
R$_1$=—OR$_3$ or —OC(=O)C(CH$_2$OR$_3$)$_2$(CH$_3$)
R$_2$=H, CH$_3$, OH or COR
R$_3$=H or C(=O)OR$_5$
R$_4$=C$_1$-C$_5$ alkyl or H
R$_5$=a saturated or unsaturated alkyl chain having 10-20 carbon atoms.
a=2-8

An example of a hydrophobic core includes mucic acid modified with lauroyl groups (M12, FIG. 1C).

As used herein, "a bioactive amphiphilic macromolecule" (bAM) is a hydrophilic-block-hydrophobic copolymer, for example, a hydrophobic carbohydrate-derived backbone modified with alkyl chains covalently bound to a hydrophilic polymer such as polyethylene glycol (PEG) (see FIG. 1C).

In another embodiment of the present invention, a bioactive amphiphilic macromolecule (bAM) is represented by the following Formula B:

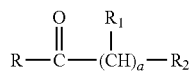

R=NHR$_4$, OR$_4$
R$_1$=—OR$_3$ or —OC(=O)C(CH$_2$OR$_3$)$_2$(CH$_3$)

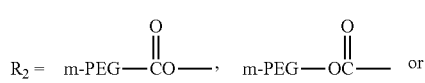

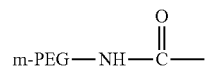

R$_3$=H, or C(=O)OR$_5$
R$_4$=C$_1$-C$_5$ alkyl, H, C$_1$-C$_3$NH$_2$, (CH$_2$)$_b$COOH, (CH$_2$)$_a$NHC(=O)(CH$_2$)$_a$R$_1$C(=O)R or C$_6$H$_4$R$_6$
R$_5$=a saturated or unsaturated alkyl chain having 10-20 carbon atoms.
R$_6$=(COOH)$_c$ or H
a=2-8
b=1-5
c=1-2

The following are additional examples of bioactive amphiphilic macromolecules:

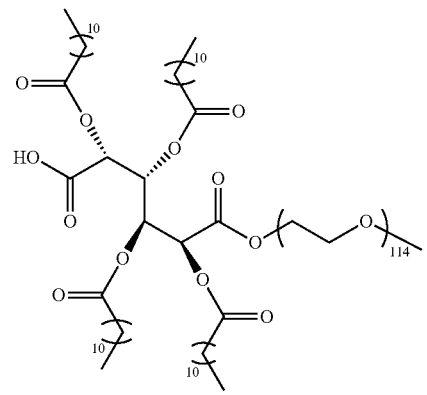

1cM
D$_h$ = 160 nm, PDI = 0.21

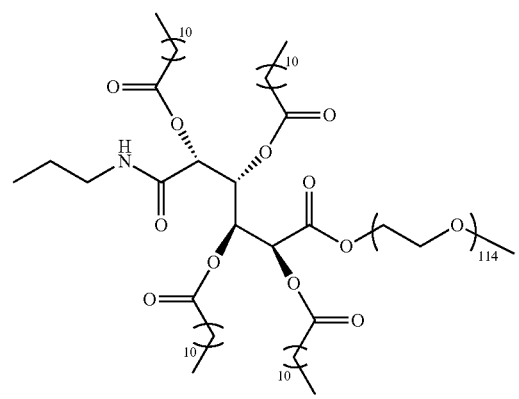

0cM
D$_h$ = 180 nm, PDI = 0.18

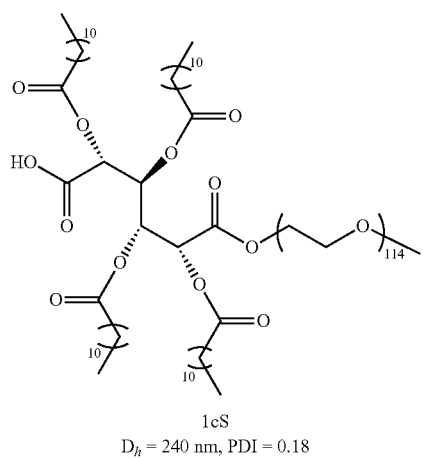

1cS
$D_h$ = 240 nm, PDI = 0.18

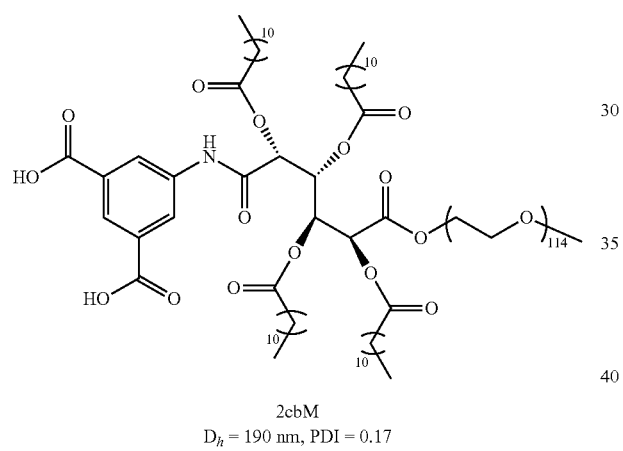

2cbM
$D_h$ = 190 nm, PDI = 0.17

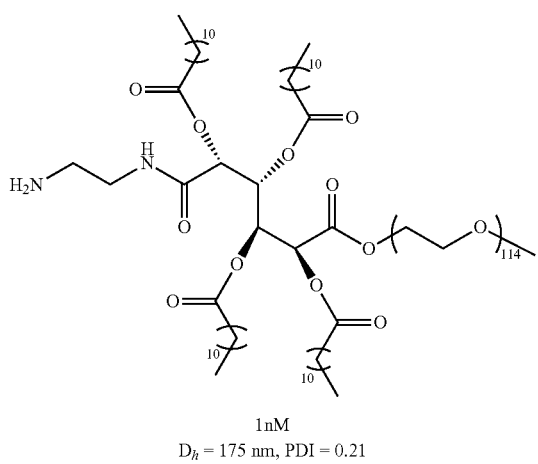

1nM
$D_h$ = 175 nm, PDI = 0.21

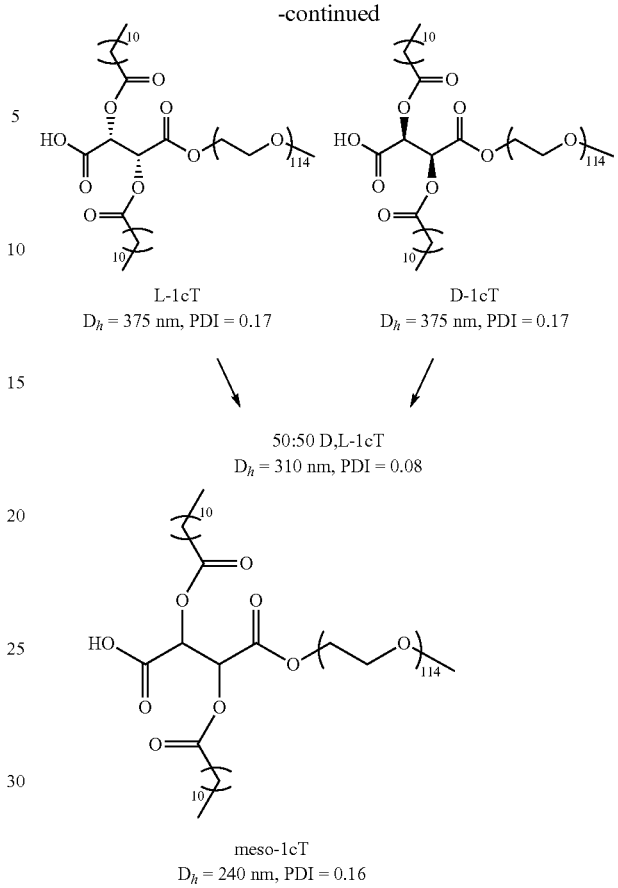

L-1cT
$D_h$ = 375 nm, PDI = 0.17

D-1cT
$D_h$ = 375 nm, PDI = 0.17

50:50 D,L-1cT
$D_h$ = 310 nm, PDI = 0.08 meso-1cT
$D_h$ = 240 nm, PDI = 0.16

As used herein: 1CM is used interchangeably with AM1.
As used herein: 0CM is used interchangeably with AM2.
As used herein: 1CM/M12 10/5 is used interchangeably with NP1.
As used herein: 1CM/M12 7/3.5 is used interchangeably with NP2.
As used herein: 1CM/PLA 10/5 is used interchangeably with NP3.
As used herein: 0CM/M12 10/5 is used interchangeably with NP4.
As used herein: 0CM/PLA 10/5 is used interchangeably with NP5.
As used herein: PEG-b-PLA/PLA 10/5 is used interchangeably with NP6.

NP Pharmaceutical Composition

The NP compositions of the invention may be formulated as a pharmaceutical composition, and may be administered to a mammalian host, such as a human patient, in a variety of forms adapted to the chosen route of administration, i.e., orally or parenterally, by intravenous, intramuscular, topical, subcutaneous, or other routes. Thus, the pharmaceutical composition of the invention may be systemically administered, e.g., orally, in combination with a pharmaceutically acceptable vehicle such as an inert diluent. They may be incorporated directly with the food of the patient's diet. For oral therapeutic administration, the compositions of the invention may be used in the form of elixirs, syrups, and the like.

Any material used in preparing any unit dosage form should be pharmaceutically acceptable and substantially non-toxic in the amounts employed. To administer the pharmaceutical composition to a patient, it is preferable to formulate the molecules in a composition comprising one or more pharmaceutically acceptable carriers. The phrase "pharmaceutically acceptable" refers to molecular entities and compositions that do not produce allergic, or other adverse reactions when administered using routes well-known in the art. "Pharmaceutically acceptable carriers" include any and all clinically useful solvents, dispersion media, coatings, antibacterial and antifungal agents, isotonic and absorption delaying agents and the like. In addition, the compositions of the invention can be formulated into sustained-release preparations and devices.

The pharmaceutical composition of the present invention can be administered to a patient by any of a number of means known in the art, including but not limited to catheterization-accompanying injections for acute treatment and drug-eluting stents, for treatment of sustained or chronic conditions.

The pharmaceutical composition of the invention may also be administered intravenously or intra-peritoneally by infusion or injection, among many other routes. Solutions may be prepared, for example, in water. However, other solvents may also be employed. Under ordinary conditions of storage and use, these preparations may contain a preservative to prevent the growth of microorganisms, and other formulation ingredients as is known in the art.

The pharmaceutical dosage forms suitable for injection or infusion should be preferably sterile, fluid and stable under the conditions of manufacture and storage. The prevention of the action of microorganisms may be brought about by various antibacterial and antifungal agents, for example, parabens, chlorobutanol, phenol, sorbic acid, thimerosal, and the like. Others are also suitable. In many cases, it may be preferable to include isotonic agents, for example, sugars, buffers or sodium chloride.

Sterile injectable solutions may be prepared by incorporating the pharmaceutical composition of the invention in the required amount into an appropriate solvent or medium with various other ingredients, e.g., those enumerated above, as needed, which may be followed by sterilization.

The above-described pharmaceutical composition containing the nanoparticles can be used to treat and/or prevent cardiovascular disease. Accordingly, the invention also features methods for treating and preventing in a subject atherosclerosis. Atherosclerosis is a disease in which plaque builds up inside your arteries. Plaque is made up of fat, cholesterol, calcium, and other substances found in the blood. Over time, plaque hardens and narrows your arteries. This limits the flow of oxygen-rich blood to your organs and other parts of your body. Atherosclerosis can affect any artery in the body, including arteries in the heart, brain, arms, legs, pelvis, and kidneys. As a result, different diseases may develop based on which arteries are affected, e.g., coronary artery disease, carotid artery disease, peripheral arterial disease, and chronic kidney disease. Atherosclerosis is also characterized by the uncontrolled scavenger-receptor mediated uptake of oxidized low-density lipoproteins (oxLDL) by macrophages and resultant athero-inflammation which leads to the formation of atherosclerotic lesions in coronary arteries.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model. A subject to be treated for atherosclerosis can be identified by standard diagnosing techniques. Typically, the terms "subject" and "patient" are used interchangeably herein in reference to a human subject.

"Treating" or "treatment" refers to administration of the nanoparticles or pharmaceutical composition to a subject or patient, who has atherosclerosis, with the purpose to cure, alleviate, relieve, remedy, delay the onset of, or ameliorate the disorder, the symptom of the disorder, the disease state secondary to the disorder, or the predisposition toward the disorder.

An "therapeutically effective amount" refers to the amount of the nanoparticles or pharmaceutical composition sufficient to effect beneficial or desired results. A therapeutically effective amount can be administered in one or more administrations, applications or dosages and is not intended to be limited to a particular formulation or administration route.

The pharmaceutical composition can be administered in vivo or ex vivo, alone or co-administered in conjunction with other drugs or therapy. As used herein, the term "co-administration" or "co-administered" refers to the administration of at least two agent(s) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, the pharmaceutical composition can be administered orally or by intravenous infusion, or injected or implanted subcutaneously, intramuscularly, intrathecally, intraperitoneally, intrarectally, intravaginally, intranasally, intragastrically, intratracheally, or intrapulmonarily.

In a further embodiment, the present invention provides a method of preventing or treating atherosclerosis comprising the steps of identifying a patient in need of such prevention or treatment, and administering to said patient a therapeutically effective amount of at least one pharmaceutical composition as described. In a further embodiment, the present invention provides a method to reduce the uptake of oxidized low-density lipoproteins in a subject by administering a therapeutically effective amount of at least one pharmaceutical composition as described.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. Variations in these dosage levels can be adjusted using standard empirical routines for optimization as is well understood in the art.

The term "biomedical device" as used herein refers to an instrumentality to be implanted into or onto a subject in order to bring about a desired result. Examples of biomedical devices, include, but are not limited to, stents, grafts, shunts, stent grafts, fistulas, angioplasty devices, balloon catheters, venous catheters, implantable drug delivery devices, adhesion barriers, hydrogels, biological polymers, microelectrodes, probes, prosthetic valve, a cardiac valve, or a venous valve and tissue scaffolds.

An embodiment of the invention includes a biomedical device containing a pharmaceutical composition comprising nanoparticles.

In a further embodiment of the invention, a pharmaceutical composition comprising nanoparticles can be immobilized onto the metal surface of atherosclerotic plaque-passivating stents for treatment of acute coronary syndromes. A pharmaceutical composition comprising nanoparticles can be directly applied onto the metal surface through phosphonate-, silinate-, or thiolate-metal linkages. The pharmaceutical composition comprising nanoparticles can be within a matrix/coating applied to the stent, for example with hydrogel systems that are spray coated onto the stent surface. The pharmaceutical composition comprising nanoparticles can be embedded in a matrix that is overlaid/coated with a diffusion-controlling membrane. As an example, the pharmaceutical composition of nanoparticles can be embedded in a poly-lactic-co-glycolic acid (PLAGA) matrix that is applied to the metal, and then overlaid with styrene-ethylene/butylene-styrene (SEBS) polymers to control water permeation in the nanoparticle/PLAGA matrix as well as control nanoparticle diffusion from the matrix.

In a further embodiment of the invention, a pharmaceutical composition comprising nanoparticles can be immobilized on balloons or other inflatable or expandable devices that may be temporarily positioned within a body to deliver a therapeutic agent and/or continuation of therapeutic agents and then removed. The therapeutic agents may include liquid formulations of NPs. This type of delivery device may be particularly advantageous in the vasculature where stents may not be suitable, for example, in the larger vessels of the peripheral vascular system. In use, the balloon or other inflatable or expandable device may be coated with one or more liquid formulations of therapeutic agent(s) and delivered to a treatment site. The act of inflation or expansion would, force the therapeutic agents into the surrounding tissue. The device may be kept in position for a period of between ten seconds to about five minutes depending upon the location. The liquid formulation comprising NPs in a pharmaceutically effective dosage, one or more pharmaceutically acceptable solubility enhancers and water in the range from about one percent by weight to about seventy percent by weight, the liquid formulation comprising a final solution of taxane in the range from about 0.05 mg/ml to about 15 mg/ml.

In a further embodiment, the pharmaceutical composition may further comprise at least one diagnostic agent or a targeting agent, or both, as well as more than one type of diagnostic agent and/or targeting agent. The diagnostic agent or a targeting agent may also be conjugated to the pharmaceutical agent with a linker.

As used herein, the term "diagnostic agent" refers to any molecule which produces, or can be induced to produce, a detectable signal. The diagnostic agent may be any diagnostically useful compound that may be bound via a functional group or linker thereon to the composition of the invention. Diagnostic moieties having reporter molecules that can be detected by imaging equipment may include radioactive, paramagnetic, fluorescent or radioopaque chemical entities. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, iodinated sugars that are used as radioopaque agents, and can be appended to linker backbones using ester or other linkages. Such methods are known to one with ordinary skill in the art.

As used herein, "targeting agents" refer to ligands, polymers, proteins, cytokines, chemokines, peptides, nucleic acids, lipids, saccharides or polysaccharides, small molecules or any combination thereof, (for example a gylcolipid, glycoprotein etc) that bind to a receptor or other molecule on the surface of a targeted cell. An exemplary of a peptide targeting agent is cell adhesion molecule 1 (VCAM-1). The degree of specificity can be modulated through the selection of the targeting molecule. For example, antibodies are very specific. These can be polyclonal, monoclonal, fragments, recombinant, or single chain, many of which are commercially available or readily obtained using standard techniques. Additional examples of peptide targeting agents include RGD peptide, EGF peptide, Intercellular Adhesion Molecule 1 (ICAM-1), glucose regulated protein 78 (GRP78) NH2-CAPGPSKSC-COOH, and VCAM-1 Cyclic peptide: NH2-CVHSPNKKC-COOH, (disulfide bridge is between the cysteine residues). Such methods are known to one with ordinary skill in the art, for example, BIOCONJUGATE TECHNIQUES (Academic Press; 1st edition, Greg T. Hermanson, 1996) describes techniques for modifying or crosslinking of biomolecules.)

As used herein, the terms "polymer," "polymeric" and similar terms have the usual meaning known to those skilled in the art and thus may be used to refer to homopolymers, copolymers (e.g., random copolymer, alternating copolymer, block copolymer, graft copolymer) and mixtures thereof.

Non-biodegradable or biodegradable polymers may be used. Representative polymers include poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly (hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups and other modifications routinely made by those skilled in the art.

As used herein, the term "linker" refers to a chemical moiety that connects a molecule to another molecule, covalently links separate parts of a molecule or separate molecules. The linker provides spacing between the two molecules or moieties such that they are able to function in their intended manner. Examples of linking groups include peptide linkers, enzyme sensitive peptide linkers/linkers, self-immolative linkers, acid sensitive linkers, multifunctional organic linking agents, bifunctional inorganic crosslinking agents, polymers and other linkers known in the art. The linker may be stable or degradable/cleavable.

In a further embodiment, the present invention provides a method to deliver a pharmaceutical composition as described to a cell expressing a scavenger receptor or a CD 36 receptor comprising contacting a cell with a pharmaceutical composition as described with at least one targeting agent. In a further embodiment, the present invention provides a method to deliver a pharmaceutical composition comprising a bAM to an atherosclerotic lesion and/or to inflammatory vasculature in a subject in need thereof comprising administering a pharmaceutical composition comprising a bAM, and may further include at least one targeting agent, as well as a diagnostic agent. The targeting agent may be VCAM-1 or ICAM-1. The types of scavenger receptors that may be targeted include class A and class B scavenger receptors, e.g. SCARA1, SCARA2, SCARA3, SCARA4, SCARA5, SCARB1, SCARB2 or SCARB3.

In a further embodiment, the present invention provides a method to detect a scavenger receptor or a CD 36 receptor on the surface of cell in vitro comprising contacting a cell in a biological sample with a pharmaceutical composition as described and at least one diagnostic agent, comparing the level detected in the biological sample to a standard level in a control sample; and determining the signal emitted in the sample. The biological sample may contain a homogenous or heterogenous collection of cells. The types of scavenger receptors that may be detected include SCARA1, SCARA2, SCARA3, SCARA4, SCARA5, SCARB1, SCARB2 or SCARB3. Depending on the type of diagnostic agent being used, one with ordinary skill in the art will adapt the proper modality to detect pharmaceutical compositions as described comprising a diagnostic agent.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference in their entireties.

The following non-limiting examples set forth herein below illustrate certain aspects of the invention.

EXAMPLES

Materials:

All chemicals/materials were purchased from Sigma-Aldrich (Milwaukee, Wis.) or Fisher Scientific (Pittsburgh, Pa.) and used as received unless otherwise noted. Bioactive amphiphilic macromolecules (AMs), termed AM 1 and AM 2, and mucic acid modified with lauroyl chloride (M12) were prepared as previously described. D,L-Lactide was recrystallized three times from distilled ethyl acetate. Poly(ethylene glycol)-block-poly(lactic acid) (PEG-b-PLA; $M_n$ of each block=5 kDa) was a gift. Heterobifunctional PEG ($M_n$=5000 g mol$^{-1}$, PDI=1.11), having primary amine protection with tert-butyloxycarbonyl at one terminus and a free primary amine at the other (t-Boc-NH$_2$-PEG$_{114}$-NH$_2$), was purchased from JenKem Technology (Beijing, China). The red hydrophobic fluorophore 2,2,10,10-Tetraethyl-6,14-bis-(triisopropylsilylethynyl)-1,3,9,11-tetraoxa-dicyclopenta[b,m]pentacene (EtTP-5) was a gift. Deionized (DI) water with a resistivity of 18 MΩ·cm was obtained using Milli-Q Water System (Millipore, Billerica, Mass.). Macrophage colony stimulating factor (M-CSF) was purchased from PeproTech (Rocky Hill, N.J.). Primary Human Coronary Artery Smooth Muscle Cells (CASMC) and Primary Human Coronary Artery Endothelial Cells (HCAEC) were purchased from Lonza (Walkersville, Md.). Human embryonic kidney cells stably transfected with human Scavenger Receptor A1 (HEK-SRA) were a gift.

PLA Homopolymer Synthesis:

PLA homopolymer ($M_n$=10,600 g mol$^{-1}$, PDI=1.02) was synthesized according to literature procedure. Briefly, all glassware was dried prior to use and reactions were carried out under dry argon. D,L-Lactide (9.90 g, 69 mmol) was dried under vacuum for 3 h, and then dissolved in 80 mL anhydrous toluene (0.86 M) under argon at 72° C., using an oil bath. Dry n-octanol (95 mg, 0.73 mmol) was added to the lactide solution and stirred for 30 min. Previously distilled tin(II) 2-ethylhexanoate (294 mg, 0.73 mmol) was dissolved in 2 mL of dry toluene and added slowly to the above solution. The ring-opening polymerization was allowed to react for 60 h at 70° C. and subsequently cooled to room temperature. Toluene was removed via rotary evaporation at 70° C. and 18 mL of dichloromethane (DCM) was added to dissolve the PLA product. PLA was purified by first precipitating into 200 mL cold hexane/ethanol (4/1, v/v) and washed twice with the cold hexane/ethanol mixture. Solvent was removed via rotary evaporation and the product was dried in vacuo. The product was then redissolved in 16 mL of DCM and precipitated into 120 mL cold methanol followed by washing with cold methanol. This process was repeated in triplicate, methanol was removed via rotary evaporation and the resulting PLA homopolymer (white solid) was dried in vacuo (7.20 g, 72% yield).

Molecular weight characteristics and PDI were determined via size exclusion chromatography (SEC) utilizing a Waters® 515 HPLC Pump, 717 plus Autosampler, 486 Tunable Absorbance Detector, and 410 Differential Refractometer and dimethylformamide (DMF) as eluent.

Fluorescent AM Synthesis:

Amine terminal, bioactive AM, specifically AM 1, was fluorescently labeled with 5(6)-carboxyfluorescein N-hydroxysuccinimide ester. First, M12 (280 mg, 0.30 mmol) was added to a round bottomed flask and dissolved in 14 mL of a DCM:DMF (5:2) solvent mixture. t-Boc-NH$_2$-PEG$_{114}$-NH$_2$ (500 mg, 0.10 mmol) was dissolved in 4 mL of DCM and subsequently added to the M12 solution. Then 320 µL of a 1M N,N'-dicyclohexylcarbodiimide (DCC) (0.32 mmol) solution in DCM was slowly added to the above reaction solution and triethylamine (TEA; 0.15 mmol) was added as a catalyst. This reaction was allowed to proceed for 48 h at room temperature. After 48 h, the reaction mixture was diluted with 20 ml DCM and washed once with 0.1N HCl and twice with brine. The organic layer was dried over MgSO$_4$ for 30 min and isolated by vacuum filtration. DCM was removed from the filtrate via rotary evaporation and the resulting oil was diluted in ~2 mL of DCM. The product was precipitated into cold diethyl ether and collected by centrifugation. The resulting white solid was washed 4 times with diethyl ether and dried in vacuo. PEGylation of the M12 functionality was confirmed by $^1$H NMR utilizing a Varian 400 MHz spectrophotometer. AM 1-NH$_2$-t-boc: $^1$H NMR (CDCl$_3$; ppm): 0.88 (t, 12H, CH$_3$), 1.30 (m, 64H, CH$_2$), 1.45 (s, 9H, CH$_3$), 1.65 (m, 8H, CH$_2$), 2.38 (m, 4H, CH$_2$), 2.60 (m, 4H, CH$_2$), 3.63 (m, ~0.45 kH, CH$_2$), 5.42 (m, 1H, CH), 5.50 (m, 1H, CH), 5.59 (m, 2H,CH).

The obtained product AM 1-tBoc (200 mg, 0.034 mmol) was added to a 20 mL vial and dissolved in 5 mL DCM and submerged in an ice bath. Next, trifluoroacetic acid (0.050 mL, 0.68 mmol) was added and the deprotection was carried out for 1 h. The reaction mixture was washed once with 0.10 N HCl and twice with brine. The organic layer was dried over $MgSO_4$ for 30 min and separated by vacuum filtration. The solvent was removed via rotary evaporation and the resulting oil was dissolved in 2 mL DCM and precipitated into cold diethyl ether. The resulting white solid was washed twice with diethyl ether and dried in vacuo. Removal of the t-boc protecting group was verified by $^1H$ NMR, as determined by the disappearance of the singlet peak centered at 1.45 ppm. All other $^1H$ NMR shifts were identical to those listed above.

Following deprotection and isolation, the amine terminated, bioactive AM (30 mg, 5.0 µmol) was dissolved in 400 µL of anhydrous DMSO and 5(6)-carboxyfluorescein N-hydroxysuccinimide ester (12 mg, 25 µmol) was dissolved in 600 µL of anhydrous DMSO. In 30 minute intervals, 67 µL of the AM solution was added to the fluorescein solution over a 3 h period to give a final AM and activated fluorescein concentration of 5.0 mm and 25 mm, respectively. A catalytic amount of TEA (5.0 µmol) was added to the AM solution prior to mixing. The reaction solution was allowed to react in the dark for 18 h at room temperature. The resulting fluorophore labeled AM was purified by dialysis against phosphate buffer saline (PBS) for 36 h followed by dialysis against deionized water for 36 h and subsequently lyophilized yielding an orange colored solid (31 mg, 97% yield).

The resulting fluorescently labeled AM was characterized by UV-vis spectroscopy using a Thermo Scientific Nano-Drop 2000C UV-vis spectrophotometer. The degree of fluorescein labeling was quantitative and calculated using an extinction coefficient of 68 000 $M^{-1}$ $cm^{-1}$, as previously reported, for free fluorescein in PBS.

Nanoparticle Fabrication:

Kinetically assembled nanoparticles (NPs) comprised of bioactive AMs or PEG-b-PLA and an organic core solute were prepared via Flash NanoPrecipitation. Typically, a confined impinging jet mixer was utilized to mix 250 µL of an aqueous stream with 250 µL of a THF stream containing 40 mg $mL^{-1}$ AM and 20 mg $mL^{-1}$ of a chosen core solute, mucic acid acylated with lauroyl groups (M12; No PEG) or poly(lactic acid) (PLA). All NP samples were prepared at an AM:core solute weight ratio of 2:1. Upon mixing, the exit stream was immediately introduced into 2 mL of DI $H_2O$ ($H_2O$:THF of 9:1) and subsequently dialyzed against DI $H_2O$ to remove residual THF. Dual fluorescent NPs comprised of AM 1 as the AM and M12 as the core were prepared using the same procedure as above. The shell of the NP was rendered fluorescent using a weight ratio of 5:1 of unlabeled to fluorescein labeled AM 1 (i.e. fluorescein labeled AM 1 is 20 wt %) and the core was made fluorescent by co-precipitating 2.3 wt % of ETTP5 relative to M12 weight. All experiments outlined below utilized NPs within two weeks of fabrication unless otherwise noted.

Dynamic Light Scattering and Zeta Potential:

Dynamic light scattering (DLS) and zeta potential measurements of fabricated NPs were performed using a Malvern-Zetasizer Nano Series DLS detector with a 22 mW He—Ne laser operating at λ=632.8 nm, an avalanche photodiode detector with high quantum efficiency, and an ALV/LSE-5003 multiple τ digital correlator electronics system. NP sizes were determined following dialysis at a concentration of 0.6 mg $mL^{-1}$ in either DI $H_2O$ or PBS at 25° C. In addition, DLS measurements to determine the size and colloidal stability of the fabricated NPs in the presence of fetal bovine serum (FBS) were carried out in RPMI media with or without 20% v/v of FBS at a NP concentration of 0.6 mg $mL^{-1}$ at 37° C. As a control, size data was also obtained on RPMI media containing solely FBS. Data analysis of DLS measurements was performed using the normal resolution mode and reported hydrodynamic diameters were obtained from intensity distributions. Zeta potential measurements were carried out at a NP concentration of 1.0 mg $mL^{-1}$ in PBS inside a zeta folded capillary cells purchased from Malvern Instruments. Samples were gently mixed with pipettes to ensure homogeneous mixing and equilibrated for 5 min at 25° C. Both DLS and zeta potential measurements were performed in triplicate.

AM Release Profile:

NPs comprised of 20 wt % fluorescein labeled AM 1, prepared as described previously, and 80 wt % unlabeled AM 1 were utilized to determine the release profile of AM 1. For the micellar system, fluorescein labeled AM 1 and unlabeled AM 1, both at 1 mM (6 mg $mL^{-1}$), were mixed in a volume ratio of fluorescently labeled to unlabeled of 20/80 v/v and sonicated for 15 min. Fluorescently labeled NPs or micelles in either 0.5 mL of PBS or 10% v/v FBS in PBS at 6.0 mg $mL^{-1}$ for NPs or 4.0 mg $mL^{-1}$ for micelles were sealed in a 300 kDa MWCO Float-A-Lyzer (Spectrum Laboratories Inc; Rancho Dominguez, Calif.) and dialyzed against 80 mL of the equivalent buffer solution at room temperature. The buffer solution was replaced three times within the first 24 h and every 24 h after. Samples were taken from the inner fluid at predetermined time intervals and measured using a Thermo Scientific NanoDrop 2000C UV-vis spectrophotometer. Percent release of the fluorescently labeled AM 1 was determined by comparing the absorbance spectrum at the predetermined time points to the absorbance spectrum prior to dialysis. UV-vis absorbance measurements were performed in triplicate.

Cell Culture:

Peripheral blood mononuclear cells (PBMC) were isolated from human buffy coats (Blood Center of New Jersey; East Orange, N.J.) by Ficoll-Paque (1.077 g $mL^{-1}$; GE Healthcare) density gradient. Monocytes were selected by plate adherence after two hours by washing thrice with PBS and cultured for 7 days in RPMI 1640 (ATCC) with 10% FBS, 1% Penicillin/Streptomycin and 50 ng $mL^{-1}$ M-CSF for differentiation into macrophages (MDM). Media was exchanged every two to three days. Primary Human Coronary Artery Smooth Muscle Cells (CASMC) (Lonza) between passages 3-6 were cultured in SM-GM2 media (Lonza). CASMC were plated on Type I Collagen coated wells for cytotoxicity experiments. Primary Human Coronary Artery Endothelial Cells (HCAEC) (Lonza) between passages 2-6 were cultured in EGM2-MV media (Lonza). HCAEC were seeded on fibronectin-coated wells for cytotoxicity experiments. Human embryonic kidney cells stably transfected with human scavenger receptor A1 (HEK-SRA) were cultured in DMEM high glucose (Lonza) supplemented with 10% FBS, 1% penicillin/streptomycin, Blasticidin and HygromycinB. SRA expression was induced through the addition of 0.25 µg $mL^{-1}$ tetracycline.

Nanoparticle Cytocompatibility:

NP cytocompatibility was determined via LIVE/DEAD assay (Invitrogen; Carlsbad, Calif.) with MDMs, CASMCs and HCAECs. Cells were treated for 24 h under 10% FBS with several NP concentrations ranging from 9 to 900 µg $mL^{-1}$, which corresponds to a bulk AM 1 concentration of $10^{-6}$ to $10^{-4}$ m respectively. After treatment, cells were stained with 2 µM calcein AM and 4 µM ethidium homodimer-1, and subsequently imaged with a Nikon Eclipse TE2000-S epifluorescent microscope. Live cells were discerned from dead cells using Image J analysis software 1.43 m. For the negative control group, cells were treated with 70% methanol for 10 minutes prior to LIVE/DEAD assay. All conditions were normalized to untreated cells and repeated in triplicate.

oxLDL Uptake by PBMC Derived Macrophages:

Human MDMs were co-incubated with 5 µg mL$^{-1}$ of 3,3'-dioctadecyloxacarbocyanine (DiO) labeled oxLDL (Kalen Biomedical; Montgomery Village, Md.) and either NPs or micelles for 24 h in the presence of 0 (serum-free), 5, 10 or 20% FBS. AM 1 concentration in both delivery systems was held constant at 10$^{-6}$ M, which corresponds to a NP concentration of 9 µg mL$^{-1}$. Cells were fixed and counterstained with Hoechst 33342 before epifluorescent imaging on a Nikon Eclipse TE2000-S. Uptake of oxLDL in MDMs was quantified by ImageJ and normalized to cell count. Analyzed data were from three independent experiments performed in triplicate.

Foam Cell Formation:

Foam cell phenotype was induced by incubating MDMs with 50 µg mL$^{-1}$ of oxLDL (Biomedical Technologies; Stoughton, Mass.) and either NPs or micelles for 48 h in the presence of 10% FBS. To maintain the AM 1 to oxLDL concentration ratio used in the DiO oxLDL uptake studies, AM 1 concentration of 10$^{-5}$ M or 60 µg mL$^{-1}$ and NP concentration of 90 µg mL$^{-1}$ was used. Cells were fixed, stained with Oil-Red-O and counterstained with Hoechst 33342. Brightfield and epifluorescent images were taken on a Nikon Eclipse TE2000-S. Cells with excessive lipid accumulation indicating the foam cell phenotype were counted relative to total population. Analyzed data were from three independent experiments performed in triplicate.

Nanoparticle-Scavenger Receptor Interactions:

HEK-SRA cells (basal and induced) were employed to investigate scavenger receptor (SR) interactions with NPs. For uptake/binding interactions cells were incubated with dual fluorescent NPs (90 µg mL$^{-1}$) for 18 h in 10% FBS media. Dual fluorescent NPs were prepared as described above. For SR-A1 blocking experiments, induced HEK-SRA cells were first incubated with either 10 µg mL$^{-1}$ SR-A1 monoclonal antibody (monoclonal mouse antihuman; R&D Systems; Minneapolis, Minn.) or polyinosinic acid for 1 h in 10% FBS media. To discern non-specific from specific binding, an IgG isotype control was included where the SR-A1 monoclonal antibody was replaced with purified mouse IgG$_1$ (Invitrogen; Carlsbad, Calif.). After 1 h, the media was removed and replaced with 10% FBS media containing dual fluorescent NPs (90 µg mL$^{-1}$) and SR-A1 mAb, IgG$_1$ isotype, or polyinosinic acid (10 µg mL$^{-1}$) for 6 h. Cells for both NP uptake/binding and SR-A1 receptor blocking were fixed and counterstained with Hoechst 33342 before imaging on a Leica TCS SP2 confocal microscope. Images were analyzed for co-localization of ETTP5, encapsulated in the NP core, and fluorescein labeled AM 1. Cell associated fluorescence due to NP binding/uptake was quantified by ImageJ and normalized to cell count.

Estimation of the Number of AM Chains per Nanoparticle:

An approximation for the number of AM 1 chains per NP 1 was determined by employing previously published results [7] and the following equation:

$$n\pi\left(\frac{\xi_i}{2}\right)^2 = 4\pi\left(\frac{D_{sphere}}{2} + \frac{\xi_i}{2}\right)^2 \qquad (1)$$

where n is the number of chains per particle, $\xi_i$ is the blob size a polymer chain occupies at the particle surface, and $D_{sphere}$ is the diameter of the polymer coated particle. Eq (1) sets the area occupied by all polymer chains equal to the total available surface area of the particle. Assuming that the attached PEG chains have an equal size to that of a free PEG chain in solution, the minimum number of chains per particle can be determined. This is referred to as the mushroom confirmation and the corresponding size ($\xi_{mushroom}$), equivalent to the "Flory size", can be calculated as follows:

$$\xi_{mushroom} = 0.76 \, Mw_{PEG}^{0.5} \, [\text{Å}] \qquad (2)$$

where $Mw_{PEG}$ is equal to the molecular weight of the PEG chain, which is 5 kDa in this report. Based on Eq (2) the blob size for a mushroom confirmation is equal to $\xi=5.40$ nm and the area occupied by each PEG chain is 23 nm$^2$ polymer$^{-1}$. To estimate the number of polymer chains, in mushroom confirmation, a volume average diameter of 150±10 nm for NP 1 was used in Eq (1). This provides an estimate of 3300 AM 1 chains particle$^{-1}$ and assuming a homogenous distribution of AM 1 and M12 during NP fabrication, ~10000 M12 molecules per NP core. It is important to note that the mushroom confirmation approximates a minimum number of chains per particle.

Estimation of a more practical blob size, $\xi_{experimental}$, can be made by utilizing experimental data reported by Prud'homme and coworkers, who first functionalized polystyrene latex spheres with PEG chains and subsequently determined the number of bound chains per particle via a Baleux assay. Accounting for the molecular weight of PEG in this report, 5 kDa, and determining the ratio of surface area between the previously reported latex sphere and the volume average diameter of NP 1, 150±10 nm, a blob size of $\xi=4.1$ nm was estimated. Based on Eq 1, this provides an estimate of 5600 AM 1 chains particle$^{-1}$ and 17000 M12 molecules per NP core.

Statistical Analysis:

DLS, AM release, and cytocompatibility results are presented as means±S.D, while all other in vitro results are presented as ±S.E.M. Data for inhibition of oxLDL uptake and foam cell formation were evaluated by one-way ANOVA and Tukey's test was used for post-hoc pairwise comparisons between individual conditions. A p-value of 0.05 or less was considered statistically significant, see FIG. 4(a)-(c).

Stabilizing AMs and the organic solutes employed in Flash NanoPrecipitation are illustrated in FIG. 1C. An example of a bioactive AM is mucic acid modified with lauroyl groups, 5 kDa poly(ethylene glycol) (PEG), and either a carboxylic acid (1CM) or propyl amide (0CM) functionality. NPs formulated with PEG-block-poly(lactic acid) (PEG-b-PLA) copolymer, where each block has a molecular weight of 5 kDa, served as a non-active control for in vitro studies. The hydrophobic solutes (FIG. 1C), which constitute the core of the NP and provide an anchoring site for the AM, implemented in these studies include mucic acid modified with lauroyl groups, termed M12, or an 11 kDa PLA. 1CM and 0CM were packaged into NPs by Flash NanoPrecipitation as depicted in FIG. 1. The rapid solvent exchange of this process leads to kinetically trapped NPs while maintaining control of core compositions. Rapid micromixing is produced by novel impinging jet micromixers as previously described. In this experiment two streams were used: a THF stream containing bioactive AM and M12 or PLA (2:1 by weight) and an anti-solvent stream of water that upon mixing produces high supersaturation. After mixing, the final H$_2$O:THF ratio was 9:1 v/v and the newly formed NPs were immediately dialyzed against MilliQ $H_2O$ to remove THF. Uniform particle size distributions were observed by DLS and hydrodynamic diameters ($D_h$) of NPs ranged from 150 to 200 nm, with the exception of the PEG-b-PLA/PLA 10/5 system, ~45 nm. $D_h$ and polydispersities (PdI) for the NPs are listed in FIG. 1C.

Nanoparticle Stability in Serum

Figure 2:
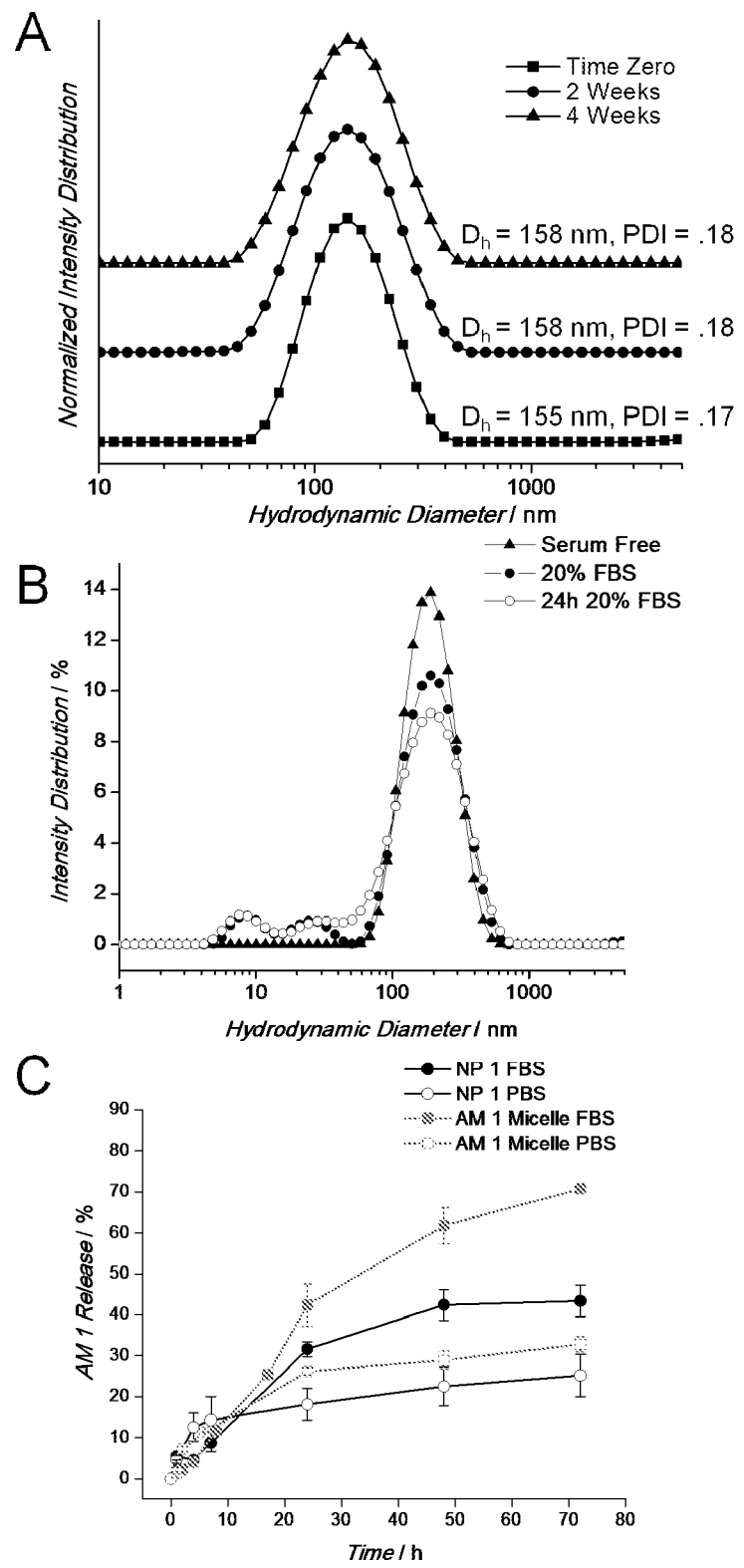
FIG. 2 shows: Kinetically assembled nanoparticles exhibit colloidal stability when stored for extended time (4 weeks) or incubated in the presence of serum proteins.
Figure 4:
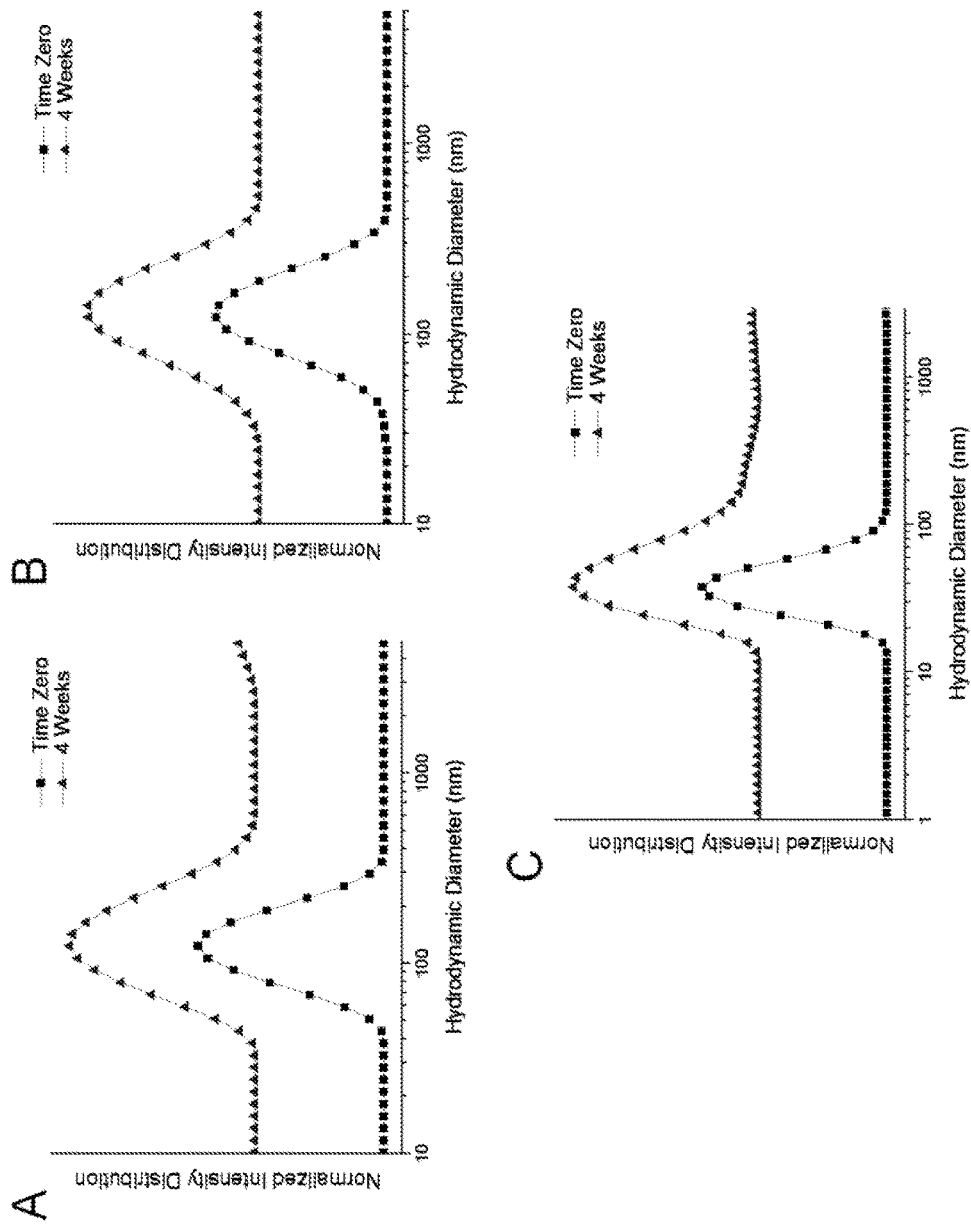
FIG. 4 shows: Intensity Distributions: Time zero (black) and 4 week (blue) intensity distributions of A) NP 3, B) NP 4, and C) NP 6 stored at 37° C.

Solution stability of the fabricated NPs upon storage and co-incubation with fetal bovine serum (FBS) was monitored by DLS (FIGS. 2 and 4). Colloidal stability of the bioactive AM NP, 1CM/M12 10/5, is displayed in FIG. 2A. No significant changes in the intensity distributions, $D_h$, or count rate relative to time zero were detected during the 37° C. 4 week incubation period, indicating extended aqueous stability of the colloids.

Since these NPs are to be utilized for managing atherosclerosis, it would be more relevant to monitor colloidal stability in the presence of serum proteins. The intensity distribution of the 1CM/M12 10/5 NP at 0.6 mg $mL^{-1}$ in RPMI media containing up to 20% FBS was measured initially and after 24 h incubation (FIG. 2B). For comparison, NPs were also incubated at 37° C. under serum-free conditions. The difference in $D_h$ between NPs dispersed in deionized water (FIG. 2A; ~160 nm) versus salt- and serum-containing RPMI media (FIG. 2B; ~190 nm) potentially arises from the shielding of the anionic charges of the M12 core and the 1CM bioactive AM by counterions. Because DLS operates on Brownian motion and determines $D_h$ from particle diffusion coefficients, interparticle repulsion in deionized water causes an artificially faster diffusion rate. This was also evident in zeta potential measurements where NP charge in deionized water was −30 mV versus −6 mV in phosphate buffer. The small distribution peaks in FIG. 2B under 100 nm can be attributed to serum proteins as reported previously. As shown in FIG. 2B, particle size was unaffected by the addition of serum protein even after 24 hours of incubation. In order to demonstrate the enhanced physiological stability of kinetically fabricated NPs versus micelles, the percent release of 1CM, under sink conditions, was monitored via dialysis against both PBS and PBS containing 10% FBS (FIG. 2C). Monitoring the release of 1CM from both systems was accomplished by fluorescently labeling the hydrophilic terminus with a reactive fluorescein molecule and measuring absorbance via UV-vis spectroscopy. Fluorescently labeled 1CM was incorporated at 20 wt % for both systems with the remainder comprising of unlabeled 1CM. In both systems, the release of 1CM was greater in the presence of FBS vs PBS. However, retention of 1CM by the NP system versus micellar system in both PBS and PBS containing 10% FBS was superior. These findings indicate that kinetic fabrication of these therapeutic AMs into NPs, rather than thermodynamically assembled micelles, provides a drug delivery platform with enhanced structural integrity upon introduction to biological fluids. See also FIG. 4.

Bioactivity in Monocyte Derived Macrophages (MDMs)

Figure 3:
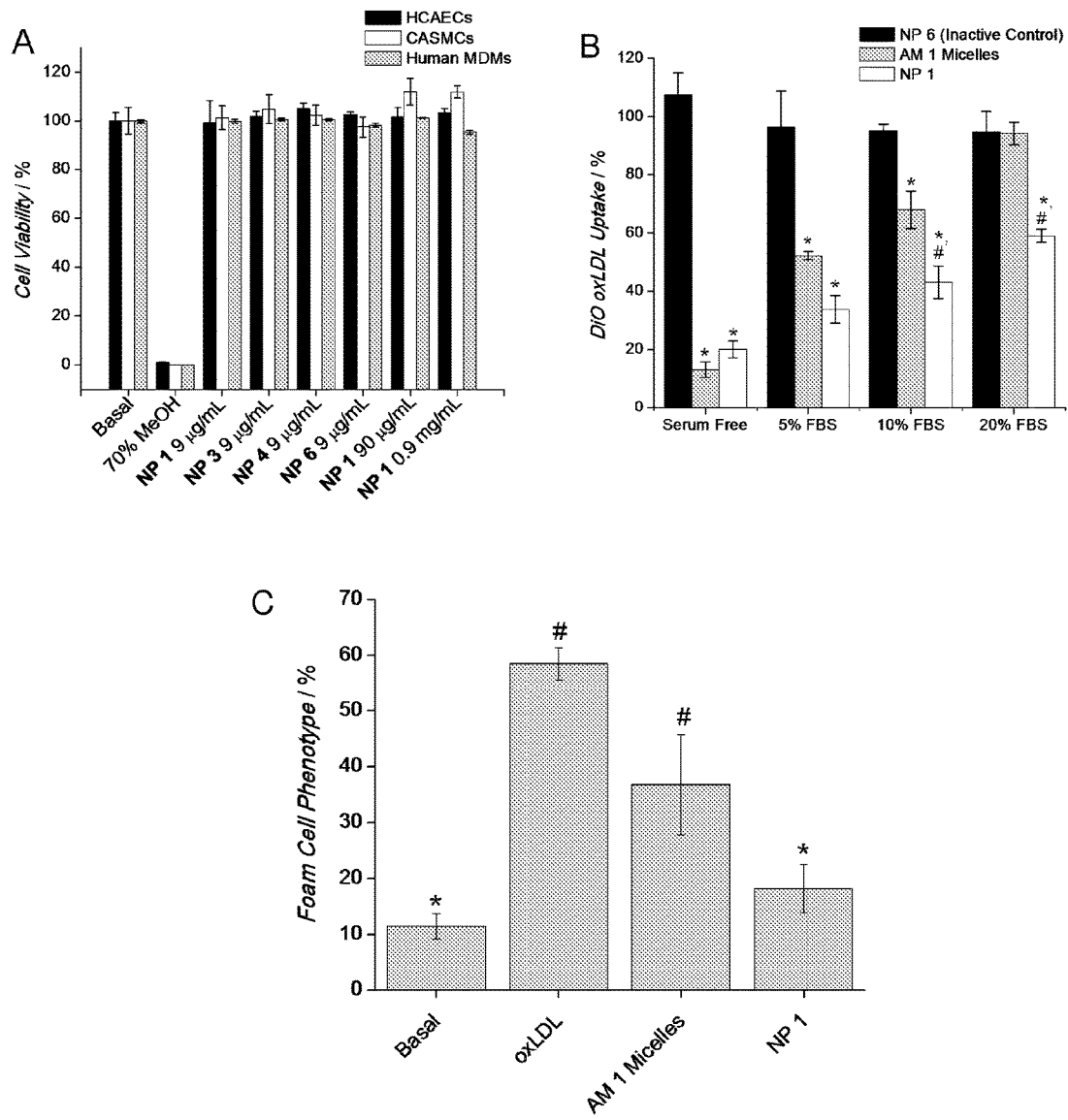
FIG. 3 shows: Nanoparticle cytocompatibility FIG. 3(A) and in vitro comparison of kinetic assembled NPs versus thermodynamic assembled micelles for inhibiting oxLDL uptake FIGs. (B) and foam cell formation FIGs. (C), a critical requisite for atherosclerotic therapies, in human MDMs (HMDM or MDM). A) Cell viability of MDMs, HCAECs and CASMCs after incubation with NPs for 24 h and 10% FBS. Experiment repeated in triplicate, error bars=±S.D.
Figure 5:
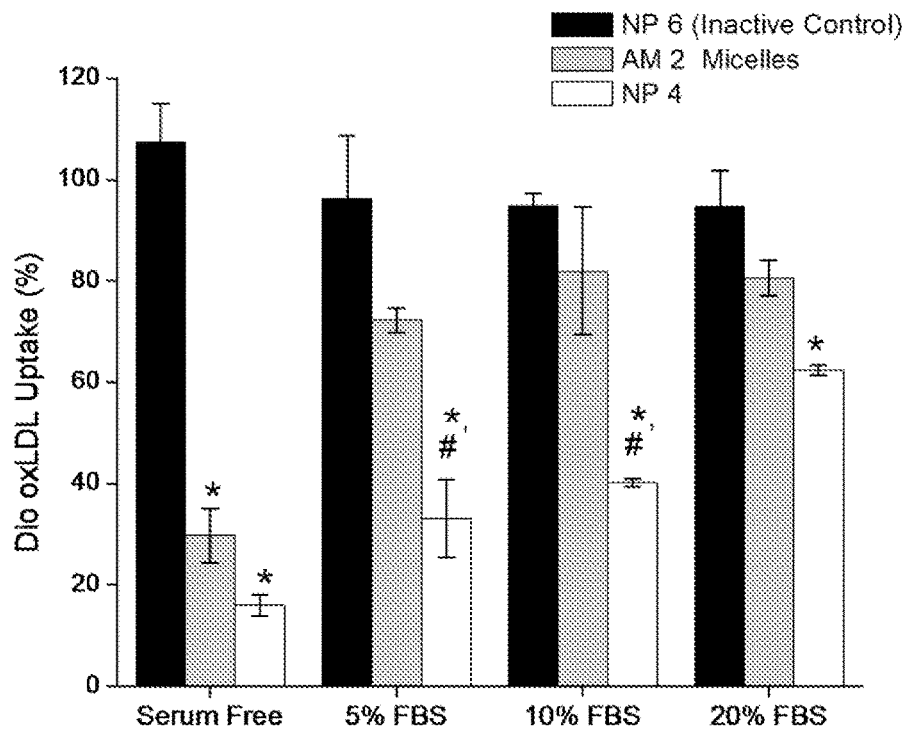
FIG. 5 shows: in vitro comparison of kinetic assembled NPs versus thermodynamic assembled micelles for inhibiting oxLDL uptake. Quantification of DiO oxLDL (5 μg mL-1) uptake by MDMs after 24 h incubation with AM 2 micelles or NP 4 NPs under 0 to 20% FBS, [AM 2]=10-6 M. NP 6 serve as an inactive control and all treatments are normalized to cells incubated exclusively with DiO oxLDL. Data are from an n=3 conducted in triplicate (error bars=±S.E.M.). Statistical significance was evaluated at p<0.05, * indicates significance versus NP 6 and # versus AM 2 micelles.
Figure 6:
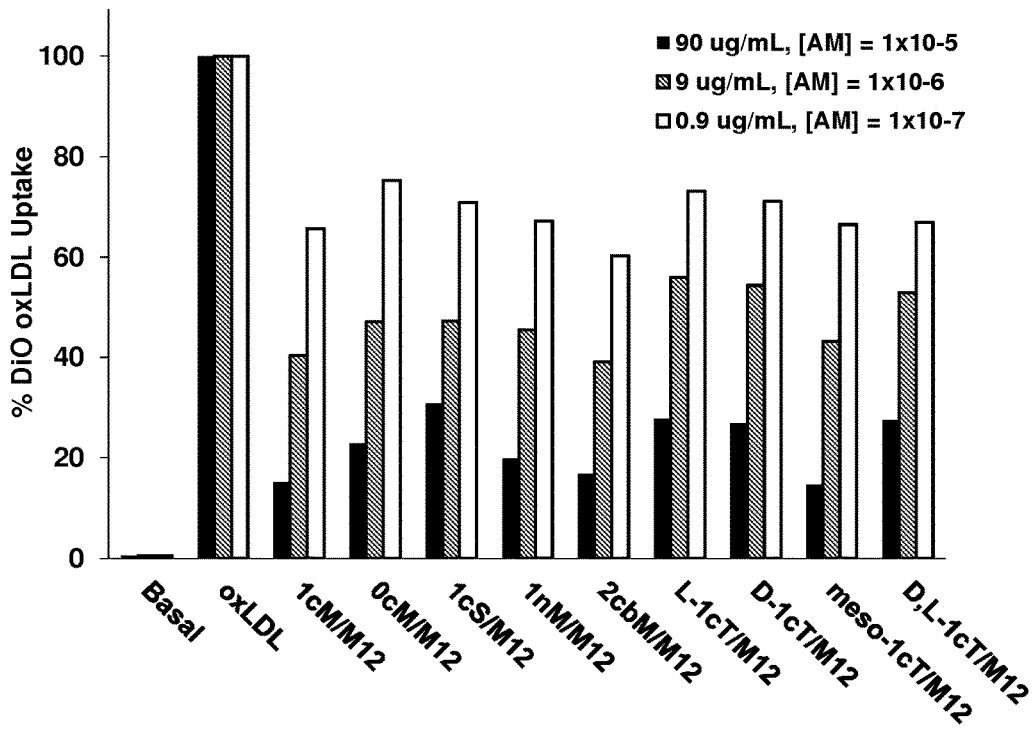
FIG. 6 shows: DiO oxLDL (5 μg/mL) uptake by human monocyte derived macrophages (HMDMs) after 24 h incubation with a given NP compositions at concentrations varying from 0.9 to 90 μg/mL. All treatments contained 10% fetal bovine serum (FBS) and are normalized to cells incubated exclusively with DiO oxLDL. This plot shows the expected NP dose dependency on inhibiting the uptake of oxLDL in HMDMs.

Prior to investigating the bioactivity of the NP versus micelle systems in human MDMs, the NP cytocompatibility was determined via LIVE/DEAD® assay, see FIGS. 3, 5 and 6. FIG. 3A shows the percent cell viability for several NP systems in three different primary cell lines. Cytocompatibility was examined not only in human MDMs, but also other atherosclerosis relevant cells, including coronary artery endothelial (HCAECs) and coronary artery smooth muscle cells (CASMCs). As seen in FIG. 3A, all tested NPs demonstrated complete cytocompatibility. Cytocompatibility for the 1CM/M12 10/5 NP system was determined at NP concentrations ranging from 9 to 900 μg $mL^{-1}$, which corresponds to a bulk 1CM concentration of $10^{-6}$ to $10^{-4}$ M, respectively.

Inhibition of oxLDL uptake in human MDMs by AM NPs and analogous micellar systems were determined (FIG. 3B-C). Human PBMC monocytes isolated from whole blood were first differentiated into macrophages using macrophage colony stimulating factor for one week prior to initiating experiments. Human MDMs were co-incubated with 5 μg $mL^{-1}$ of 3,3'-dioctadecyloxacarbocyanine (DiO)-labeled oxLDL and either NPs or micelles for 24 h in the presence of 0 (serum free), 5, 10 or 20% FBS. Uptake of oxLDL in MDMs was determined by ImageJ analysis of epifluorescent images. Results for 1CM/M12 NP and the 1CM micelle systems are displayed in FIG. 3B, where all conditions were normalized to MDMs only receiving DiO-labeled oxLDL.

1CM concentration in both delivery systems was $10^{-6}$ M, which corresponds to a NP concentration of 9 μg $mL^{-1}$. As shown in FIG. 3B, NP and micelle vehicles exhibited similar inhibition of oxLDL uptake when MDMs were treated under serum-free conditions. However, as FBS concentration was increased to 20%, the efficacy of the micelles decreased to 6% while 1CM/M12 NPs maintained more than 40% inhibition of oxLDL uptake. Retention of bioactivity for the NP system can be attributed to a slower rate of partitioning to surrounding serum proteins as the bioactive AM is kinetically anchored to the NP core through favorable hydrophobic interactions. In contrast, the micelle system loses bioactivity in the presence of serum proteins which can disrupt the micelle organization causing premature release of the bioactive AM. A significant difference in oxLDL uptake between 1CM/M12 NPs and the traditional micelle system, as determined by one way ANOVA and subsequent post-hoc analysis, is evident at conditions incubated with 10% FBS ($p<0.05$) and 20% ($p<0.01$). Visual evidence is provided in FIG. 3C, which clearly shows the level of fluorescence in each system is similar under serum-free conditions, but is significantly weaker when cells are treated with 1CM/M12 10/5 NPs under 20% FBS. Fluorescent images for DiO oxLDL uptake alone and other serum-containing conditions for 1CM/M12 10/5 NPs and 1CM micelles are available in Figure SX. It is important to note that M12 had no therapeutic efficacy towards inhibiting oxLDL uptake as determined by co-incubating MDMs with PEG-b-PLA NPs loaded with M12 and DIO oxLDL. Furthermore, the inhibition of DiO oxLDL uptake under serum-free conditions is similar for both the 1CM/M12 NP and 1CM micelle systems suggesting that M12 itself has no bioactivity. The NP system sustains bioactivity in the presence of serum protein.

Cholesterol Assessment in Macrophages

Excessive accumulation of cholesterol through intimal macrophage uptake of modified LDLs results in a visible departure from the cell's native morphology. Excess cholesterol leads to the formation of numerous intracellular lipid droplets, thus giving the cell a "foam-like" appearance. Cell formation is associated with the development of atherosclerotic plaque. Cell formation was examined in human MDMs while in the presence of the 1CM/M12 10/5 NPs (FIG. 3C). Foam cell phenotype was induced by incubating MDMs with 50 μg $mL^{-1}$ of oxLDL and either NPs or micelles for 48 h in the presence of 10% FBS. To maintain the 1CM to oxLDL concentration ratio used in the DiO oxLDL uptake studies above, a 1CM concentration of $10^{-5}$ M, equivalent to 90 μg/mL for the NP, was implemented. Intracellular lipids were made visible by postfixation staining with Oil Red O.

After staining, foam cells were marked red and subsequently counted via image analysis software. It was determined that the percentage of foam cells for the oxLDL alone condition was near 60±3%, while MDMs incubated with 1CM/M12 10/5 NPs reduced foam cell formation close to the basal level with statistical significance (p<0.05), 18±4%, versus 12±2%. Notably, foam cell formation in MDMs receiving treatment with 1CM micelles did not display statistical significance from MDMs incubated with oxLDL. This result further corroborates the DiO oxLDL studies and demonstrates that the method used to package the bAMs, micelles versus kinetically formed NPs, has a significant influence on bioactivity in the presence of serum proteins.

Nanoparticle Affinity and Scavenger Receptors

Macrophagic scavenger receptors (SRs) have been identified and implicated in the unregulated uptake of oxLDL. Class A and B scavenger receptors account for 75 to 90% uptake of modified LDLs. One such receptor is the scavenger receptor A1 (SR-A1). affinity of 1CM/M12 NPs with SRs was validated in human embryonic kidney (HEK) cells engineered to express SR-A1 (HEK-SRA). Dual fluorescent NPs were prepared via Flash NanoPrecipitation utilizing fluorescein labeled 1CM, incorporated at 20 wt % of total 1CM weight, and by co-precipitating a highly hydrophobic red fluorophore, (ETTP5), with M12. Cells with and without SR-A1 expression were incubated with fluorescent 1CM/M12 10/5 NPs for 24 h. Confocal images that were taken and analyzed showed the level of NP associated fluorescence is significantly increased in SR-A1 expressing cells relative to non-expressing cells. Furthermore, NP specificity towards SR-A1 was confirmed via receptor blocking experiments. SR-A1 expressing cells solely incubated with fluorescent NPs resulted in a high level of cell associated fluorescence; however, when cells were incubated with polyinosinic acid, a known SR-A1 ligand, prior to the addition of fluorescent NPs, cell associated fluorescence was nearly abolished. These results provide strong visual evidence that the 1CM/M12 NP system displays affinity towards SR-A1. To discern non-specific from specific binding, SR-A1 monoclonal antibody was replaced with purified mouse $IgG_1$ (FIG. 4E) as an isotype control. When SR-A1 was blocked with antibody, cell associated fluorescence decreased ~50%, as evidenced from fluorescence microscopy, in comparison to the isotype control. In addition, blocking SR-A1 with PIA reduced cell associated NP fluorescence ~95%.

Figure 7:
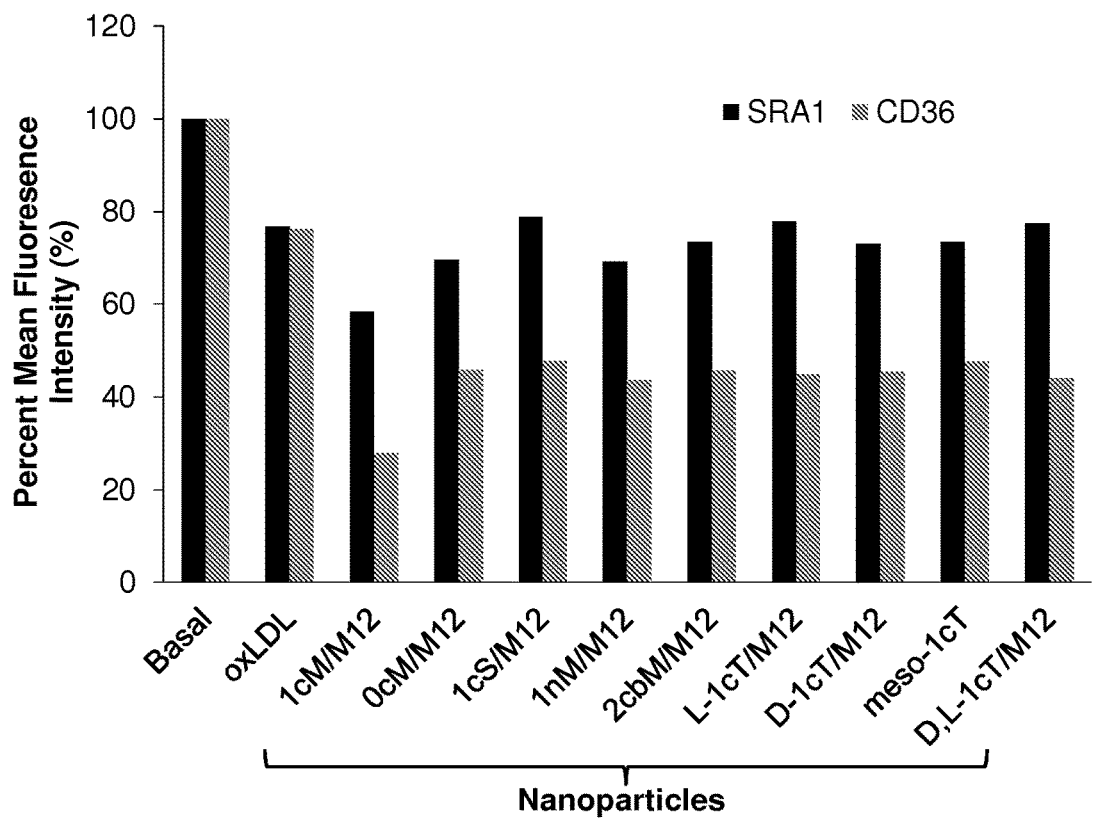
FIG. 7 depicts: in vitro comparison of several NP compositions on either blocking or reducing the cell surface expression of scavenger receptors A1 and CD36 (a class B scavenger receptor) on human monocyte derived macrophages (HMDMs).

Role of Nanoparticles on Binding to Macrophages with Variable SRA1/CD36 Expression FIG. 7 depicts in vitro comparison of several NP compositions on either blocking or reducing the cell surface expression of scavenger receptors A1 and CD36 (a class B scavenger receptor) on human monocyte derived macrophages (HMDMs). These results were obtained via flow cytometry following the incubation of human monocyte derived macrophages (HMDMs) with 5 μg $mL^{-1}$ oxLDL and 90 μg $mL^{-1}$ of a given NP ([AM]=$10^{-5}$ M) composition for 24 h at 37° C. Prior to flow cytometry, cell surface SR-A1 and CD36 receptors were marked with fluorescently labeled primary antibodies and the cells were fixed in 1% paraformaldehyde (PFA). The results depicted in FIG. 7, provide further evidence that these nanoparticles either bind/block scavenger receptors and/or reduce scavenger receptor expression. Furthermore, this is the first evidence that the formulated NPs may have an influence on scavenger receptors like CD36, another major receptor in the uptake of modified LDL particles and the plaque development in atherosclerotic lesions.

Nanoparticles Targeted to Atherosclerotic Lesions and Inflammatory Vasculature

Reaction pathway was developed for the conjugation of vascular cellular adhesion molecule-1 (VCAM-1) targeting peptide to 1 cM employing maleimide-thiol chemistry.

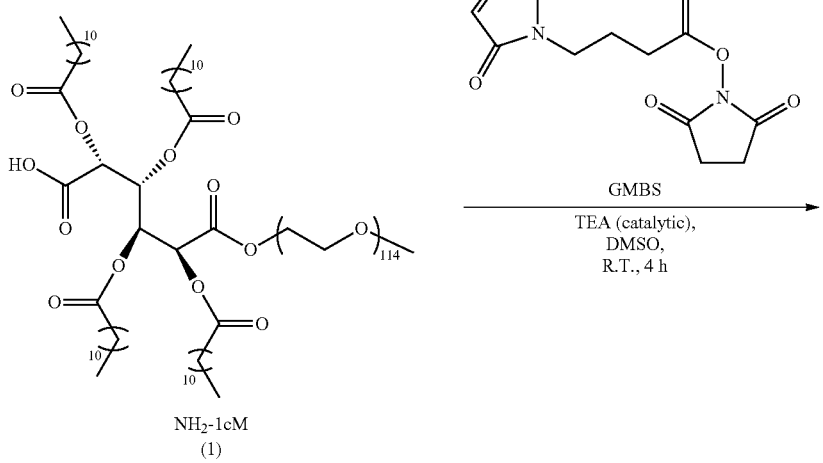

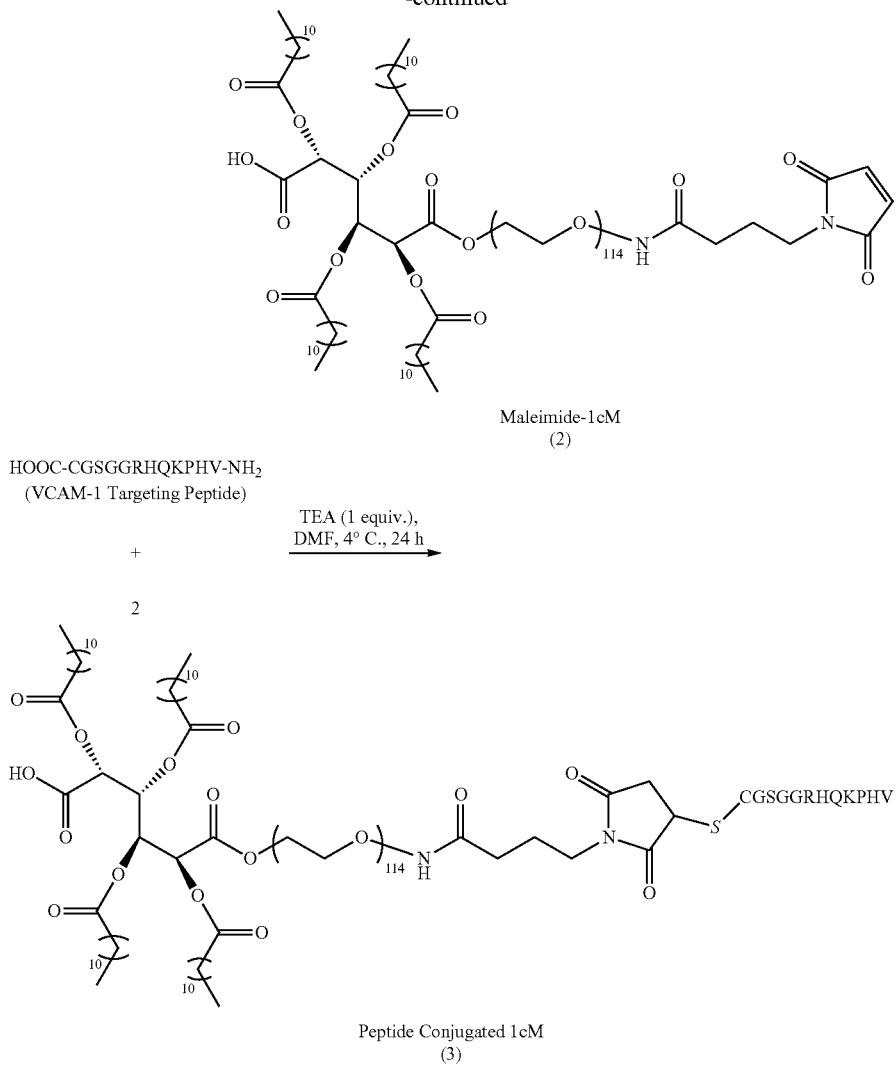

Maleimide-1cM
(2)

HOOC-CGSGGRHQKPHV-NH₂
(VCAM-1 Targeting Peptide)

+

2

TEA (1 equiv.),
DMF, 4° C., 24 h
→

Peptide Conjugated 1cM
(3)

Abbreviations: N-β-Maleimidobutyryl-oxysuccinimide ester (GMBS), Triethylamine (TEA), dimethylsulfoxide (DMSO), dimethylformamide (DMF), and room temperature (R.T.). The incorporation of product 3 into formulated 1 cM NPs has allowed the cell specific delivery of the NPs in vivo to inflamed endothelial cells associated with progressing atherosclerotic lesions. An atherosclerotic Apo-E-deficient mouse model was used in these preliminary experiments.

Synthesis:

Synthesis of Maleimide-1 cM (2): The amine terminated, NH2-1 cM (1) (35 mg, 5.8 μmol) was dissolved in 400 μL of anhydrous DMSO and N-γ-Maleimidobutyryl-oxysuccinimide ester (GMBS; 8.2 mg, 29 μmol) was dissolved in 760 μL of anhydrous DMSO. In 30 minute intervals, 100 μL of the 1 solution was added to the GMBS solution over a 1.5 h period to give a final 1 and GMBS concentration of 5.0 mM and 25 mM, respectively. An equivalent of TEA (5.8 μmol) was added to the 1 solution prior to mixing. The reaction solution was allowed to react in the dark for 4 h at room temperature. The resulting Maleimide-1 cM (2) was purified by dialysis against acidic deionized (DI) water for 24 h and subsequently lyophilized yielding a white solid (32 mg, 89% yield). Reaction of 1 with GMBS was confirmed by 1H NMR utilizing a Bruker 500 MHz spectrophotometer. 2:1H NMR (CDCl3; ppm): 0.88 (t, 12H, CH3), 1.30 (m, 64H, CH2), 1.65 (m, 8H, CH2), 2.38 (m, 4H, CH2), 2.60 (m, 4H, CH2), 3.63 (m, ~0.45 kH, CH2), 5.42 (m, 1H, CH), 5.50 (m, 1H, CH), 5.59 (m, 2H,CH), 6.70 (s, 1.6H, CH=CH). A coupling efficiency of ~80% was determined by integration of the methylene-proton resonance of PEG at 3.63 ppm and the proton resonance of the maleimide carbon-carbon double bond at 6.70 ppm.

Synthesis of Peptide Conjugated 1 cM (3): Maleimide-1 cM (2) (10 mg, 1.6 μmol) and VCAM-1 targeting peptide (2.1 mg, 1.7 μmol) with an amino acid sequence of HOOC-CGSGGRHQKPHV-NH2 were dissolved in 333 μL of anhydrous DMF to give a final 2 and VCAM-1 peptide concentration of 5.0 mM. An equivalent of TEA (1.6 μmol) was added as a catalyst. The reaction solution was allowed to react in the dark for 4 h at room temperature and then 16 h at 4° C. Following reaction any unreacted maleimide moieties were quenched by the addition of 2 equivalents of β-mercaptoethanol (3.2 μmol). The reaction solution was then precipitated into cold diethyl ether and the precipitate was washed thrice with cold diethyl ether. The precipitate was collected through centrifugation and the ether was discarded. The precipitate was allowed to dry in the atmosphere for 20 min and then dissolved in 1 mL of deionized water. The product was isolated using two 3.5 k MWCO Amicon 0.5 mL centrifugal device. The product was washed 4 times with a total of 4 mL deionized water and the retentate was collected and diluted to 5 mL and subsequently lyophilized yielding a white solid (8.1 mg, 72% yield). VCAM-1 peptide conjugation was confirmed by both a colorimetric assay and matrix assisted laser desorption ionization time-of-flight (MALDI-ToF) mass spectrometry. The degree of conjugation was determined to be ~50% using a primary amine colorimetric assay, trinitrobenzene sulfonic acid (TNBS), and measuring the absorption at 420 nm. A Thermo Scientific NanoDrop 2000C UV-vis spectrophotometer was employed for obtaining UV-vis spectra.

UV-vis spectroscopy and MALDI-ToF mass spectrometry were used to verify the successful conjugation between Maleimide-1 cM (2) and VCAM-1 peptide ($NH_2$—VHP-KQHRGGSGC-COOH). Ellman's assay on VCAM-1 targeting peptide before and 24 h after reaction between VCAM-1 targeting peptide and 2. A decreased absorbance at 412 nm after 24 h indicates a lower thiol concentration due to reaction with 2. Trinitrobenzene sulfonic acid (TNBS) assay for measuring primary amines on 2 (50 μM) and VCAM-1 peptide conjugated 1 cM (3) (50 μM). Absorbance at 420 nm correlates to primary amine concentration. MALDI-ToF mass spectra of before (2) and after (3) conjugation with VCAM-1 targeting peptide (MW=1262 g $mol^{-1}$). A clear shift to a higher mass/charge (m/z) ratio can be seen indicating bioconjugation was successful.

Synthesis of Alexa Fluor 750-1 cM:
Following deprotection and isolation, the amine terminated, bioactive AM (10 mg, 1.7 μmol) was dissolved in 100 μL of anhydrous DMSO and Alexa Fluor® 750 carboxylic acid, succinimidyl ester (2.2 mg, 1.7 μmol) was dissolved in 230 μL of anhydrous DMSO. In 30 minute intervals, 30 μL of the AM solution was added to the Alexa Fluor 750 solution over a 2 h period to give a final AM and fluorophore concentration of 5.0 mM. A catalytic amount of TEA (1.7 μmol) was added to the AM solution prior to mixing. The reaction solution was allowed to react in the dark for 18 h at room temperature. The resulting fluorophore labeled AM was purified by dialysis against phosphate buffer saline (PBS) for 12 h followed by dialysis against deionized water for 24 h and subsequently lyophilized yielding a teal colored solid (10 mg, 82% yield).

The resulting fluorescently labeled AM was characterized by UV-vis spectroscopy using a Thermo Scientific Nano-Drop 2000C UV-vis spectrophotometer. The degree of Alexa Fluor 750 labeling was calculated using an extinction coefficient of 240 000 M-1 cm-1, as previously reported, for free Alexa Fluor 750 and found to be ~65%.

Fluorescently Labeled and VCAM-1 Targeted Nanoparticle Formulation:
Kinetically assembled nanoparticles (NPs) comprised of VCAM-1 peptide-1 cM conjugate and/or Alexa Fluor 750-1 cM conjugate and an organic core solute were prepared via Flash NanoPrecipitation. A confined impinging jet mixer was utilized to mix 500 μL of a phosphate buffered saline (PBS) stream with 500 μL of a THF stream containing 40 mg mL-1 1 cM and 20 mg mL-1 of M12, mucic acid acylated with lauroyl groups (M12; No PEG). Upon mixing, the exit stream was immediately introduced into 4 mL of PBS (PBS:THF of 9:1) and subsequently dialyzed against PBS to remove residual THF. For passively targeted NPs, the shell of the NP was rendered fluorescent using 10 mol % of Alexa Fluor 750-1 cM conjugate with the remainder being unmodified 1 cM. For targeting atherosclerotic lesions, the shell of the NPs was comprised of 5 mol % VCAM-1 peptide-1 cM conjugate, 10 mol % Alexa Fluor 750-1 cM conjugate and 85 mol % unmodified 1 cM. For both targeted and untargeted NPs samples were prepared at 1 cM:core solute weight ratio of 2:1.

Detecting Atherosclerotic Lesions and Inflammatory Vasculature in vivo

The $ApoE^{-/-}$ transgenic model is widely used for atherosclerosis research due to high serum cholesterol levels and spontaneous development of atherosclerotic lesions when fed a high fat (western) diet. ApoE mice at approximately 4 weeks of age were fed a high fat diet (Harlan Teklad TD.88137) for 28 weeks before the experiment to develop stage V lesions. BALB/c mice of similar age, fed a standard diet, were used as a non-lesion control. To test the ability of AMs to localize to areas of spontaneous atherosclerotic lesions, mice were imaged live at multiple time points and ex vivo using a Carestream MS FX Pro (750/790 nm ex/em filter for fluorescence imaging, Xray for anatomy). One day prior to experimentation, mice were treated with chemical depilatory to remove hair. Mice were anesthetized with isoflurane (5% induction, 2% maintenance) by inhalation for imaging and administration of nanoparticles, that ranged approximately 140 nm to 160 nm in diameter. After background images were taken, mice were given tail vein injections (7.5 mL/kg body weight) of $5*10^{-4}M$ fluorescent nanoparticles. Four conditions were tested: 1) BALB/c, no injection; 2) VCAM-1 targeted nanoparticles in BALB/c; 3) untargeted nanoparticles in ApoE; 4) targeted nanoparticles in ApoE. Mice were imaged live at t0, 5 min, 30 min, 1 hr, 2.5 hr, 5 hr, 7.5 hr, 12 hr, 20 hr, 24 hr, and 27 hr post injection. After the 27 hour timepoint, mice were sacrificed by rapid exsanguination via cardiac puncture and PBS perfusion under anesthesia. Ex vivo aortas 27 hours post injection: 1) BALB/c, no injection; 2) targeted nanoparticles in BALB/c; 3) untargeted nanoparticles in ApoE; 4) VCAM-1 targeted nanoparticles in ApoE. Top: Xray. Bottom: 750/790 nm ex/em fluorescence. Significantly higher fluorescence intensity was seen with targeted nanoparticles, indicating specific localization to lesions.

What is claimed is:
1. A nanoparticle consisting of a hydrophobic core and a bioactive amphiphilic macromolecule coating said core and comprising a hydrophobic segment and a hydrophilic segment; wherein said nanoparticle comprises a single hydrophobic phase consisting of said hydrophobic core and said hydrophobic segment of the bioactive amphiphilic macromolecule; wherein the hydrophobic core and the bioactive amphiphilic macromolecule are selected so said hydrophobic core and the hydrophobic segment of said bioactive amphiphilic macromolecule are miscible in the hydrophobic phase, wherein said hydrophobic core consists of Formula A:

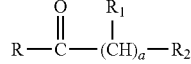

R=—$NHR_4$ or —$OR_4$
$R_1$=—$OR_3$ or —OC(=O)C($CH_2OR_3$)$_2$($CH_3$)
$R_2$=H, $CH_3$, OH or COR
$R_3$=H or C(=O)$OR_5$
$R_4$=$C_1$-$C_5$ alkyl or H $R_5$=a saturated or unsaturated alkyl chain having 10-20 carbon atoms
a=2-8
wherein said bioactive amphiphilic macromolecule consists of Formula B:

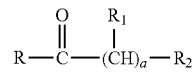

$R$=$NHR_4$, $OR_4$
$R_1$=—$OR_3$ or $OC(=O)C(CH_2OR_3)_2(CH_3)$

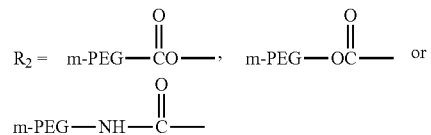

$R_3$=H, or $C(=O)R_5$
$R_4$=$C_1$-$C_5$ alkyl, H, $C_1$-$C_3NH_2$, $(CH_2)_bCOOH$, or $C_6H_4R_6$
$R_5$=a saturated or unsaturated alkyl chain having 10-20 carbon atoms
$R_6$=COOH or H
b=1-5.

2. The nanoparticle of claim 1 wherein said bioactive amphiphilic macromolecule to hydrophobic core ratio by weight is 2:1.

3. The nanoparticle of claim 1 wherein the diameter of the nanoparticle ranges from about 100 nm to about 500 nm.

* * * * *

UNITED STATES PATENT AND TRADEMARK OFFICE
CERTIFICATE OF CORRECTION

| | |
|---|---|
| PATENT NO. | : 10,016,517 B2 |
| APPLICATION NO. | : 14/237974 |
| DATED | : July 10, 2018 |
| INVENTOR(S) | : Adam W. York et al. |

It is certified that error appears in the above-identified patent and that said Letters Patent is hereby corrected as shown below:

In the Specification

Column 1, Lines 10-15 Delete the Statement Regarding Federally Sponsored Research and replace with:
This invention was made with government support under grant numbers EB005583, HL093753 awarded by the National Institutes of Health. The government has certain rights in the invention.

Signed and Sealed this
Third Day of October, 2023

*Katherine Kelly Vidal*

Katherine Kelly Vidal
*Director of the United States Patent and Trademark Office*